US006177463B1

(12) United States Patent
Gerdes et al.

(10) Patent No.: US 6,177,463 B1
(45) Date of Patent: Jan. 23, 2001

(54) OXIME DERIVATIVES AND THEIR USE AS PESTICIDES

(75) Inventors: Peter Gerdes, Aachen; Herbert Gayer, Monheim; Bernd-Wieland Krüger, Bergisch Gladbach; Bernd Gallenkamp, Wuppertal; Heinz-Wilhelm Dehne, Bonn; Stefan Dutzmann, Hilden; Gerd Hänssler, Leverkusen; Klaus Stenzel, Düsseldorf, all of (DE)

(73) Assignee: Bayer Aktiengesellschaft, Leverkusen (DE)

( * ) Notice: Under 35 U.S.C. 154(b), the term of this patent shall be extended for 0 days.

(21) Appl. No.: 08/702,597

(22) PCT Filed: Feb. 27, 1995

(86) PCT No.: PCT/EP95/00708

§ 371 Date: Sep. 3, 1996

§ 102(e) Date: Sep. 3, 1996

(87) PCT Pub. No.: WO95/24383

PCT Pub. Date: Sep. 14, 1995

(30) Foreign Application Priority Data

Mar. 10, 1994 (DE) .................................................. 44 08 006
Apr. 29, 1994 (DE) .................................................. 44 14 986
Jun. 24, 1994 (DE) .................................................. 44 22 154

(51) Int. Cl.$^7$ ...................... C07C 255/00; C07C 259/06; A01N 37/18; A01N 37/34

(52) U.S. Cl. .......................... 514/524; 514/561; 514/562; 514/599; 514/602; 514/603; 514/617; 514/618; 514/619; 514/620; 558/411; 558/413; 558/414; 562/434; 562/435; 562/437; 562/438; 564/74; 564/162; 564/163; 564/164; 564/166; 564/180; 564/183; 564/256; 564/257

(58) Field of Search ...................................... 564/256, 257, 564/162, 163, 164, 166, 180, 183, 74; 514/640; 558/411, 413, 414; 562/434, 435, 437, 438

(56) References Cited

FOREIGN PATENT DOCUMENTS

| 0 039 168 | 11/1981 | (EP) . |
| 0 174 046 | 3/1986 | (EP) . |
| 0 273 432 | 7/1988 | (EP) . |
| 0 477 631 | 4/1992 | (EP) . |
| 2039474 | 8/1980 | (GB) . |
| WO 93/07116 | 3/1993 | (WO) . |
| WO 94/00422 | 1/1994 | (WO) . |

OTHER PUBLICATIONS

AM Chemical Abstracts, vol. 120, no. 6, Feb. 7 1994, Columbus, Ohio, US; abstract no. 55101k, J.C. Jung et al. 'Model studies on the structure of poly(amideoximes) and their cyclodehydration reactions leading to poly(1,2,4–oxadiazoles).' p. 7; col. 1; see abstract & J. Polym. Sci. Part A. Poly. Chem., vol. 31, no. 3, 1993, pp. 3351–9.

*Primary Examiner*—Alan L. Rotman
(74) *Attorney, Agent, or Firm*—Norris, McLaughlin & Marcus, P.A.

(57) ABSTRACT

The invention relates to new oxime derivatives, to a plurality of processes for their preparation, and to their use as pesticides.

7 Claims, No Drawings

OXIME DERIVATIVES AND THEIR USE AS PESTICIDES

The invention relates to new oxime derivatives, to a plurality of processes for their preparation, and to their use as pesticides.

It is known that various substitutive alkoximino- and alkoxymethylene acetamides have fungicidal properties (cf., for example, EP-A 398 692, EP-A 468 775, DE-A 40 30 038 and WO-A 92/13 830).

However, the activity of these prior-art compounds is not entirely satisfactory in all fields of application, in particular when low application rates and concentrations are used.

New oxime derivatives of the general formula (I)

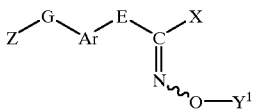

have been found,
in which
  Ar represents in each case optionally substituted arylene or heteroarylene,
  E represents a direct bond, or a 1-alkene-1,1-diyl group which has a radical $R^1$ in the 2-position, or represents a 2-aza-1-alkene-1,1-diyl group which has a radical $R^2$ in the 2-position, or represents a 3-aza-1-propene-2,3-diyl group which has a radical R in the 3-position and a radical $R^1$ in the 1-position, or represents a 1-aza-1-propene-2,3-diyl group which has a radical $R^2$ in the 1-position, or represents a 1,3-diaza-1-propene-2,3-diyl group which has a radical R in the 3-position and a radical $R^2$ in the 1-position, or represents an optionally substituted imino group ("azamethylene", N—$R^3$),
where
  R represents alkyl,
  $R^1$ represents hydrogen, halogen, cyano, or in each case optionally substituted alkyl, alkoxy, alkylthio, alkylamino or dialkylamino,
  $R^2$ represents hydrogen, amino, cyano, or in each case optionally substituted alkyl, alkoxy, alkylamino or dialkylamino, and
  $R^3$ represents hydrogen, cyano, or in each case optionally substituted alkyl, alkenyl, alkinyl, cycloalkyl or cycloalkylalkyl,
  G represents oxygen, or represents alkanediyl, alkenediyl, oxaalkenediyl or alkinediyl, each of which is optionally substituted by halogen, hydroxyl, alkyl, halogenoalkyl or cycloalkyl, or represents one of the following groups
    —Q—CQ—, —CQ—Q—, —CH$_2$—Q—; —Q—CH$_2$—, —CQ—Q—CH$_2$—, —CH$_2$—Q—CQ—, —Q—CQ—CH$_2$—, —Q—CQ—Q—CH$_2$—, —N=N—, —S(O)$_n$—, —CH$_2$—S(O)$_n$—, —CQ—, —S(O)$_n$—CH$_2$—, —C($R^4$)=N—O—, —C($R^4$)=N—O—CH$_2$—, —N($R^5$)—, —CQ—N($R^5$)—, —N($R^5$)—CQ—, —Q—CQ—N($R^5$)—, —N=C($R^4$)—Q—CH$_2$—, —CH$_2$—O—N=C($R^4$)—, —N($R^5$)—CQ—Q—, —CQ—N($R^5$)—CQ—Q—, —N($R^5$)—CQ—Q—CH$_2$—, —CQ—CH$_2$— or —N=N—C($R^4$)=N—O—,
  where
    n represents the numbers 0, 1 or 2,
    Q represents oxygen or sulfur,
    $R^4$ represents hydrogen, cyano, or in each case optionally substituted alkyl, alkoxy, alkylthio, alkylamino, dialkylamino or cycloalkyl, and
    $R^5$ represents hydrogen, hydroxyl, cyano, or in each case optionally substituted alkyl, alkoxy or cycloalkyl,
  X represents the groups —O$X^1$, —S$X^1$, —SO$X^1$, —SO$_2X^1$ or —N$X^2X^3$ where
    $X^1$, $X^2$ and $X^3$ independently of one another represent hydrogen, or in each case optionally substituted alkyl, cycloalkyl, aryl or heterocyclyl, or
    $X^2$ and $X^3$ together with the nitrogen atom form an optionally substituted heterocycle,
  $Y^1$ represents hydrogen, or in each case optionally substituted alkyl, cycloalkyl, aryl or heterocyclyl, and
  Z represents in each case optionally substituted alkyl, alkenyl, alkinyl, cycloalkyl, aryl, aryloxy, arylthio, arylamino, heterocyclyl, heterocyclyloxy, heterocyclylthio or heterocyclylamino.

Furthermore, it has been found that the new oxime derivatives of the general formula (I) are obtained by a process which comprises
a) reacting thiocarbonyl derivatives of the general formula (II)

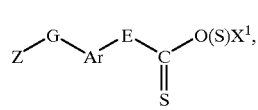

in which
  Ar, E, G, $X^1$ and Z have the abovementioned meanings, with hydroxylamine derivatives of the general formula (III)

in which
  $Y^1$ has the abovementioned meaning,
or with their acid addition salts, if appropriate in the presence of a diluent and if appropriate in the presence of a reaction auxiliary; or
b) alkylating amide derivatives of the general formula (IV)

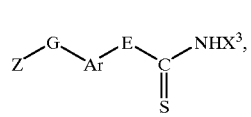

in which
  Ar, E, G, $X^3$ and Z have the abovementioned meanings, in the customary manner and reacting the resulting imino derivatives of the formula (IVa)

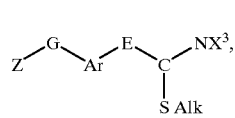

in which
  Ar, E, G, $X^3$ and Z have the abovementioned meanings and
  Alk represents alkyl, preferably methyl,
if appropriate without isolation, with hydroxylamine derivatives of -the general formula (III) or with their acid addition salts, if appropriate in the presence of a diluent and if appropriate in the presence of a reaction auxiliary; or c) alkylating amide derivatives of the general formula (V)

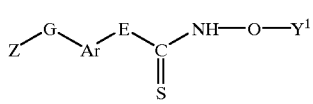

(V)

in which

Ar, E, G, $Y^1$ and Z have the abovementioned meanings, in the customary manner and reacting the resulting oximes of the formula (Va)

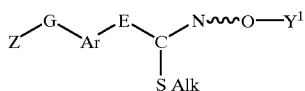

(Va),
in which

Ar, E, G, $Y^1$, Z and Alk have the abovementioned meanings, if appropriate without isolation, with amines of the general formula (VI)

$HNX^2X^3$ (VI), in which $X^2$ and $X^3$ have the abovementioned meanings, if appropriate in the presence of a diluent.

Compounds of the formula (I) where $X=SOX^1$ or $SO_2X^1$ are obtained by oxidizing corresponding compounds of the formula (I) where $X=SX^1$ in the generally customary manner, such as, for example, by oxidation by means of hydrogen peroxide or organic peracids.

Finally, it has been found that the new oxime derivatives of the general formula (I) show a very potent fungicidal activity.

If appropriate, the compounds according to the invention may exist in the form of mixtures of various isomeric forms which are possible, in particular in the form of E and Z isomers, but, if appropriate, also in the form of optical isomers and diastereomers. Claimed are the E as well as the Z isomers and also any mixtures of all other isomers which are possible.

The invention preferably relates to compounds of the formula (I), in which

Ar represents in each case optionally substituted phenylene or naphthylene, or represents heteroarylene having 5 or 6 ring members of which at least one represents oxygen, sulfur or nitrogen and, if appropriate, one or two further ring members represent nitrogen, the substituents which are possible preferably being selected from the list which follows: halogen, cyano, nitro, amino, hydroxyl, formyl, carboxy, carbamoyl, thiocarbamoyl, in each case straight-chain or branched alkyl, alkoxy, alkylthio, alkylsulfinyl or alkylsulfonyl, each of which has 1 to 6 carbon atoms, in each case straight-chain or branched alkenyl, alkenyloxy or alkinyloxy, each of which has 2 to 6 carbon atoms, in each case straight-chain or branched halogenoalkyl, halogenoalkoxy, halogenoalkylthio, halogenoalkylsulfinyl or halogenoalkylsulfonyl, each of which has 1 to 6 carbon atoms and 1 to 13 identical or different halogen atoms, in each case straight-chain or branched halogenoalkenyl or halogenoalkenyloxy, each of which has 2 to 6 carbon atoms and 1 to 13 identical or different halogen atoms, in each case straight-chain or branched alkylamino, dialkylamino, alkylcarbonyl, alkylcarbonyloxy, alkoxycarbonyl, alkylsulfonyloxy, hydroximinoalkyl or alkoximinoalkyl, each of which has 1 to 6 carbon atoms in the individual alkyl moieties, or represents in each case divalent alkylene or dioxyalkylene, each of which has 1 to 6 carbon atoms and each of which is optionally monosubstituted or polysubstituted by identical or different substituents from the series consisting of halogen and/or straight-chain or branched alkyl having 1 to 4 carbon atoms and/or straight-chain or branched halogenoalkyl having 1 to 4 carbon atoms and 1 to 9 identical or different halogen atoms, E represents a direct bond or one of the groups which follow

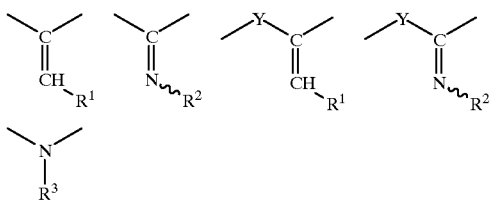

in which

Y represents oxygen, sulfur, methylene ($CH_2$) or alkylimino (N—R),

R represents alkyl having 1 to 6 carbon atoms, $R^1$ represents hydrogen, halogen, cyano, or represents alkyl, alkoxy, alkylthio, alkylamino or dialkylamino, each of which have 1 to 6 carbon atoms in the alkyl radical and each of which is optionally substituted by halogen, cyano or $C_1$–$C_4$-alkoxy, $R^2$ represents hydrogen, amino, cyano, or represents alkyl, alkoxy, alkylamino or dialkylamino, each of which have 1 to 6 carbon atoms in the alkyl radical and each of which is optionally substituted by halogen, cyano or $C_1$–$C_4$-alkoxy, and $R^3$ represents hydrogen, cyano, or represents alkyl, alkenyl or alkinyl, each of which has up to 6 carbon atoms and each of which is optionally substituted by halogen, cyano or $C_1$–$C_4$-alkoxy, or represents cycloalkyl or cycloalkylalkyl having 3 to 6 carbon atoms in the cycloalkyl moieties and, where appropriate, 1 to 4 carbon atoms in the alkyl moiety, each of which is optionally substituted by halogen, cyano, carboxyl, $C_1$–$C_4$-alkyl or $C_1$–$C_4$-alkoxycarbonyl, G represents oxygen, or represents alkanediyl, alkenediyl, oxaalkenediyl and alkindiyl, each of which has up to 4 carbon atoms and each of which is optionally substituted by halogen, hydroxyl, $C_1$–$C_4$-alkyl, $C_1$–$C_4$-halogenoalkyl or $C_3$–$C_6$-cycloalkyl, or represents one of the groups which follow
—Q—CQ—, —CQ—Q—, —$CH_2$—Q—;
—Q—$CH_2$—, —CQ—Q—$CH_2$—, —$CH_2$—Q—CQ—, —Q—CQ—$CH_2$—, —Q—CQ—Q—$CH_2$—, —N═N—, —S(O)$_n$—, —$CH_2$—S(O)$_n$—, —CQ—, —S(O)$_n$—$CH_2$—, —C($R^4$)═N—O—, —C($R^4$)═N—O—$CH_2$—, —N($R^5$)—, —CQ—N($R^5$)—, —N($R^5$)—CQ—, —Q—CQ—N($R^5$)—, —N═C($R^4$)—Q—CH2—, —$CH_2$—O—N═C($R^4$)—, —N($R^5$)—CQ—Q—, —CQ—N($R^5$)—

CQ—Q—, —N(R$^5$)—CQ—Q—CH$_2$—, —CQ—CH$_2$— or —N=N—C(R$^4$)=N—O—, in which n represents the numbers 0, 1 or 2, Q represents oxygen or sulfur, R$^4$ represents hydrogen, cyano, or represents alkyl, alkoxy, alkylthio, alkylamino or dialkylamino, each of which has 1 to 6 carbon atoms in the alkyl groups and is optionally substituted by halogen, cyano or C$_1$–C$_4$-alkoxy, or represents cycloalkyl having 3 to 6 carbon atoms which is optionally substituted by halogen, cyano, carboxyl, C$_1$–C$_4$-alkyl or C$_1$–C$_4$-alkoxy-carbonyl, and R$^5$ represents hydrogen, hydroxyl, cyano, or represents alkyl having 1 to 6 carbon atoms which is optionally substituted by halogen, cyano or C$_1$–C$_4$-alkoxy, or represents cycloalkyl having 3 to 6 carbon atoms which is optionally substituted by halogen, cyano, carboxyl, C$_1$–C$_4$-alkyl or C$_1$–C$_4$-alkoxy-carbonyl, X represents the groups —OX$^1$, —SX$^1$, —SOX$^1$, —SO$_2$X$^1$ or —NX$^2$X$^3$, in which X$^1$, X$^2$ and X$^3$ independently of one another represent hydrogen, or represent alkyl having 1 to 8 carbon atoms which is optionally substituted by halogen, cyano, hydroxyl, amino, C$_1$–C$_4$-alkoxy, C$_1$–C$_4$-alkylthio, C$_1$–C$_4$-alkylsulfinyl or C$_1$–C$_4$-alkylsulfonyl (which are in each case optionally substituted by halogen), or represent cycloalkyl having 3 to 6 carbon atoms which is optionally substituted by halogen, cyano, carboxyl, phenyl (which is optionally substituted by halogen, cyano, C$_1$–C$_4$-alkyl, C$_1$–C$_4$-halogenoalkyl, C$_1$–C$_4$-alkoxy or C$_1$–C$_4$-halogenoalkoxy), C$_1$–C$_4$-alkyl or C$_1$–C$_4$-alkoxycarbonyl, or represent in each case optionally substituted phenyl, naphthyl or (optionally benzo-fused) heterocyclyl having 5 or 6 ring members, of which at least one represents oxygen, sulfur or nitrogen and, if appropriate, one or two further ring members represent nitrogen, the substituents which are possible preferably being selected from the list which follows:

oxygen (as a replacement for two geminal hydrogen atoms), halogen, cyano, nitro, amino, hydroxyl, formyl, carboxyl, carbamoyl, thiocarbamoyl, in each case straight-chain or branched alkyl, alkoxy, alkylthio, alkylsulfinyl or alkylsulfonyl, each of which has 1 to 6 carbon atoms, in each case straight-chain or branched alkenyl or alkenyloxy, each of which has 2 to 6 carbon atoms, in each case straight-chain or branched halogenoalkyl, halogenoalkoxy, halogenoalkylthio, halogenoalkylsulfinyl or halogenoalkylsulfonyl, each of which has 1 to 6 carbon atoms and 1 to 13 identical or different halogen atoms, in each case straight-chain or branched halogenoalkenyl or halogenoalkenyloxy, each of which has 2 to 6 carbon atoms and 1 to 13 identical or different halogen atoms, in each case straight-chain or branched alkylamino, dialkylamino, alkylcarbonyl, alkylcarbonyloxy, alkoxycarbonyl, alkylsulfonyloxy, hydroximinoalkyl or alkoximinoalkyl, each of which has 1 to 6 carbon atoms in the individual alkyl moieties, in each case divalent alkylene or dioxyalkylene, each of which has 1 to 6 carbon atoms and each of which is optionally monosubstituted or polysubstituted by identical or different substituents from the series consisting of halogen and/or straight-chain or branched alkyl having 1 to 4 carbon atoms and/or straight-chain or branched halogenoalkyl having 1 to 4 carbon atoms and 1 to 9 identical or different halogen atoms; or cycloalkyl having 3 to 6 carbon atoms, heterocyclyl or heterocyclyl-methyl having in each case 3 to 7 ring members, of which in each case 1 to 3 are identical or different hetero atoms—in particular nitrogen, oxygen and/or sulfur—, and also phenyl, phenoxy, benzyl, benzyloxy, phenylethyl or phenylethyloxy, each of which is optionally monosubstituted or polysubstituted in the phenyl moiety by identical or different substituents from the series consisting of halogen, cyano and/or straight-chain or branched alkyl having 1 to 4 carbon atoms and/or straight-chain or branched halogenoalkyl having 1 to 4 carbon atoms and 1 to 9 identical or different halogen atoms and/or straight-chain or branched alkoxy having 1 to 4 carbon atoms and/or straight-chain or branched halogenoalkoxy having 1 to 4 carbon atoms and 1 to 9 identical or different halogen atoms, or X$^2$ and X$^3$ together with the nitrogen atom form a 3- to 8-membered ring, Y$^1$ represents hydrogen, or represents alkyl having 1 to 8 carbon atoms which is optionally substituted by halogen, cyano, hydroxyl, amino, C$_1$–C$_4$-alkoxy, C$_1$–C$_4$-alkylthio, C$_1$–C$_4$-alkylsulfinyl or C$_1$–C$_4$-alkylsulfonyl (which are in each case optionally substituted by halogen), or represents cycloalkyl having 3 to 6 carbon atoms which is optionally substituted by halogen, cyano, carboxyl, phenyl (which is optionally substituted by halogen, cyano, C$_1$–C$_4$-alkyl, C$_1$–C$_5$-halogenoalkyl, C$_1$–C$_4$-alkoxy or C$_1$–C$_4$-halogenoalkoxy), C$_1$–C$_4$-alkyl or C$_1$–C$_4$-alkoxycarbonyl, or represents in each case optionally substituted phenyl, naphthyl or (optionally benzo-fused) heterocyclyl having 5 or 6 ring members, of which at least one represents oxygen, sulfur or nitrogen, and, if appropriate, one or two further ring members represent nitrogen, the substituents which are possible preferably being selected from the list which follows:

oxygen (as a replacement for two geminal hydrogen atoms), halogen, cyano, nitro, amino, hydroxyl, formyl, carboxyl, carbamoyl, thiocarbamoyl, in each case straight-chain or branched alkyl, alkoxy, alkylthio, alkylsulfinyl or alkylsulfonyl, each of which has 1 to 6 carbon atoms, in each case straight-chain or branched alkenyl or alkenyloxy, each of which has 2 to 6 carbon atoms, in each case straight-chain or branched halogenoalkyl, halogenoalkoxy, halogenoalkylthio, halogenoalkylsulfinyl or halogenoalkylsulfonyl, each of which has 1 to 6 carbon atoms and 1 to 13 identical or different halogen atoms, in each case straight-chain or branched halogenoalkenyl or halogenoalkenyloxy, each of which has 2 to 6 carbon atoms and 1 to 13 identical or different halogen atoms, in each case straight-chain or branched alkylamino, dialkylamino, alkylcarbonyl, alkylcarbonyloxy, alkoxycarbonyl, alkylsulfonyloxy, hydroximinoalkyl or alkoximinoalkyl, each of which has 1 to 6 carbon atoms in the individual alkyl moieties, in each case divalent alkylene or dioxyalkylene, each of which has 1 to 6 carbon atoms and each of which is optionally monosubstituted or polysubstituted by identical or different substituents from the series consisting of halogen and/or straight-chain or branched alkyl having 1 to 4 carbon atoms and/or straight-chain or branched halogenoalkyl having 1 to 4 carbon atoms and 1 to 9 identical or different halogen atoms; or cycloalkyl having 3 to 6 carbon atoms, heterocyclyl or heterocyclyl-methyl having in each case 3 to 7 ring members, of which in each case 1 to 3 are identical or different hetero atoms—in particular nitrogen, oxygen and/or sulfur—, and also phenyl, phenoxy, benzyl, benzyloxy, phenylethyl or phenylethyloxy, each of which is optionally monosubstituted or polysubstituted in the phenyl moiety by identical or different substituents from the series consisting of halogen, cyano and/or straight-chain or branched alkyl having 1 to 4 carbon atoms and/or straight-chain or branched halogenoalkyl having 1 to 4 carbon atoms and 1 to 9 identical or different halogen atoms and/or straight-chain or branched alkoxy having 1 to 4 carbon atoms and/or straight-chain or branched halogenoalkoxy having 1 to 4 carbon atoms and 1 to 9 identical or different halogen atoms, Z represents alkyl having 1 to 8 carbon atoms which is optionally substituted by halogen, cyano, hydroxyl, amino, $C_1$–$C_4$-alkoxy, $C_1$–$C_4$-alkylthio, $C.$-$C_4$-alkylsulfinyl or $C_1$–$C_4$-alkylsulfonyl (which are in each case optionally substituted by halogen), or represents cycloalkyl having 3 to 6 carbon atoms which is optionally substituted by halogen, cyano, carboxyl, phenyl (which is optionally substituted by halogen, cyano, $C_1$–$C_4$-alkyl, $C_1$–$C_4$-halogenoalkyl, $C_1$–$C_4$-alkoxy or $C_1$–$C_4$-halogenoalkoxy), $C_1$–$C_4$-alkyl or $C_1$–$C_4$-alkoxycarbonyl, or represents in each case optionally substituted phenyl, phenoxy, phenylthio, phenylamino, naphthyl, naphthyloxy, naphthylthio, naphthylamino or (optionally benzo-fused) heterocyclyl, heterocyclyloxy, heterocyclylthio and heterocyclylamino, each of which has 5 or 6 ring members, of which at least one represents oxygen, sulfur or nitrogen, and, if appropriate, one or two further ring members represent nitrogen, the substituents which are possible preferably being selected from the list which follows:

oxygen (as a replacement for two geminal hydrogen atoms), halogen, cyano, nitro, amino, hydroxyl, formyl, carboxyl, carbamoyl, thiocarbamoyl, in each case straight-chain or branched alkyl, alkoxy, alkylthio, alkylsulfinyl or alkylsulfonyl, each of which has 1 to 6 carbon atoms, in each case straight-chain or branched alkenyl or alkenyloxy, each of which has 2 to 6 carbon atoms, in each case straight-chain or branched halogenoalkyl, halogenoalkoxy, halogenoalkylthio, halogenoalkylsulfinyl or halogenoalkylsulfonyl, each of which has 1 to 6 carbon atoms and 1 to 13 identical or different halogen atoms, in each case straight-chain or branched halogenoalkenyl or halogenoalkenyloxy, each of which has 2 to 6 carbon atoms and 1 to 13 identical or different halogen atoms, in each case straight-chain or branched alkylamino, dialkylamino, alkylcarbonyl, alkylcarbonyloxy, alkoxycarbonyl, alkylsulfonyloxy, hydroximinoalkyl or alkoximinoalkyl, each of which has 1 to 6 carbon atoms in the individual alkyl moieties, in each case divalent alkylene or dioxyalkylene, each of which has 1 to 6 carbon atoms and each of which is optionally monosubstituted or polysubstituted by identical or different substituents from the series consisting of halogen and/or straight-chain or branched alkyl having 1 to 4 carbon atoms and/or straight-chain or branched halogenoalkyl having 1 to 4 carbon atoms and 1 to 9 identical or different halogen atoms; or cycloalkyl having 3 to 6 carbon atoms, heterocyclyl or heterocyclyl-methyl having in each case 3 to 7 ring members, of which in each case 1 to 3 are identical or different hetero atoms—in particular nitrogen, oxygen and/or sulfur—, and also phenyl, phenoxy, benzyl, benzyloxy, phenylethyl or phenylethyloxy, each of which is optionally monosubstituted or polysubstituted in the phenyl moiety by identical or different substituents from the series consisting of halogen, cyano and/or straight-chain or branched alkyl having 1 to 4 carbon atoms and/or straight-chain or branched halogenoalkyl having 1 to 4 carbon atoms and 1 to 9 identical or different halogen atoms and/or straight-chain or branched alkoxy having 1 to 4 carbon atoms and/or straight-chain or branched halogenoalkyl having 1 to 4 carbon atoms and 1 to 9 identical or different halogen atoms.

The saturated or unsaturated hydrocarbon chains in the definitions, such as alkyl, alkanediyl, alkenyl or alkinyl, also in connection with hetero atoms such as in alkoxy, alkylthio or alkylamino, are in each case straight-chain or branched.

Halogen generally represents fluorine, chlorine, bromine or iodine, preferably fluorine, chlorine or bromine, in particular fluorine or chlorine.

In particular, the invention relates to compounds of the formula (I), in which

Ar represents in each case optionally substituted ortho-, meta- or para-phenylene, or represents furandiyl, thiophenediyl, pyrrolediyl, pyrazolediyl, triazolediyl, oxazolediyl, isoxazolediyl, thiazolediyl, isothiazolediyl, oxadiazolediyl, thiadiazolediyl, pyridinediyl, pyrimidinediyl, pyridazinediyl, pyrazinediyl, 1,3,4-triazinediyl or 1,2,3-triazinediyl, the substituents which are possible being selected, in particular, from the list which follows:

fluorine, chlorine, cyano, methyl, ethyl, trifluoromethyl, methoxy, ethoxy, methylthio, methylsulfinyl or methylsulfonyl, E represents one of the groups which follow

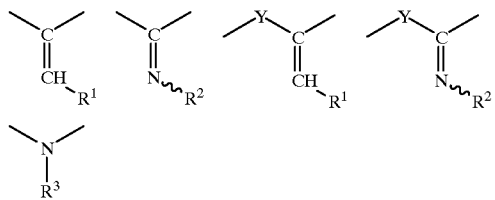

in which

Y represents oxygen, sulfur, methylene ($CH_2$) or alkylimino (N—R),

R represents methyl, ethyl, n- or i-propyl, or n-, i- or s-butyl, $R^1$ represents hydrogen, fluorine, chlorine, bromine, cyano, or represents methyl, ethyl, propyl, methoxy, ethoxy, methylthio, ethylthio, methylamino, ethylamino or dimethylamino, each of which is optionally substituted by fluorine, chlorine, cyano, methoxy or ethoxy, $R^2$ represents hydrogen, amino or cyano, or represents methyl, ethyl, methoxy, ethoxy, methylamino, ethylamino or dimethylamino, each of which is optionally substituted by fluorine, chlorine, cyano, methoxy or ethoxy, and $R^3$ represents hydrogen, cyano, or represents methyl, ethyl, n- or i-propyl or n-, i- or s-butyl, each of which is optionally substituted by fluorine, cyano, methoxy or ethoxy, or represents allyl or propargyl, or represents cyclopropyl, cyclobutyl, cyclopentyl, cyclohexyl, cyclopropylmethyl, cyclobutylmethyl, cyclopentylmethyl or cyclohexylmethyl, each of which is optionally substituted by fluorine, chlorine, cyano, carboxyl, methyl, ethyl, n- or i-propyl, methoxy-carbonyl or ethoxy-carbonyl, G represents oxygen, or represents methylene, dimethylene(ethane-1,2-diyl), ethene-1,2-diyl or ethine-1,2-diyl, each of which is optionally substituted by fluorine, chlorine, hydroxyl, methyl, ethyl, n- or i-propyl, trifluoromethyl, cyclopropyl, cyclobutyl, cyclopentyl or cyclohexyl, or represents one of the groups which follow
—Q—CQ—, —CQ—Q—, —CH$_2$—Q—, —Q—CH$_2$—, —CQ—Q—CH$_2$—, —CH$_2$—Q—CQ—, —Q—CQ—CH$_2$—, —Q—CQ—Q—CH$_2$—, —N=N—, —S(O)$_n$—, —CH$_2$—S(O)$_n$—, —CQ—, —S(O)$_n$—CH$_2$—, —C($R^4$)=N—O—, —C($R^4$)=N—O—CH$_2$—, —N($R^5$)—, —CQ—N($R^5$)—, —N($R^5$)—CQ—, —Q—CQ—N($R^5$)—, —N=C($R^4$)—Q—CH$_2$—, —CH$_2$—O—N=C($R^4$)—, —N($R^5$)—CQ—Q—, —CQ—N($R^5$)—CQ—Q— or —N($R^5$)—CQ—Q—CH$_2$— in which
n represents the numbers 0, 1 or 2,
Q represents oxygen or sulfur, $R^4$ represents hydrogen or cyano, or represents methyl, ethyl, n- or i-propyl, n-, i- or s-butyl, methoxy, ethoxy, propoxy, butoxy, methylthio, ethylthio, propylthio, butylthio, methylamino, ethylamino, propylamino, dimethylamino or diethylamino, each of which is optionally substituted by fluorine, chlorine, cyano, methoxy or ethoxy, or represents cyclopropyl, cyclobutyl, cyclopentyl or cyclohexyl, each of which is optionally substituted by fluorine, chlorine, cyano, carboxyl, methyl, ethyl, n- or i-propyl, methoxycarbonyl or ethoxy-carbonyl, and $R^5$ represents hydrogen, hydroxyl or cyano, or represents methyl, ethyl, n- or i-propyl or n-, i-, s- or t-butyl, each of which is optionally substituted by fluorine, chlorine, cyano, methoxy or ethoxy, or represents cyclopropyl, cyclobutyl, cyclopentyl or cyclohexyl, each of which is optionally substituted by fluorine, chlorine, cyano, carboxyl, methyl, ethyl, n- or i-propyl, methoxy-carbonyl or ethoxycarbonyl, X represents the groups —O$X^1$, —S$X^1$, —SO$X^1$, —SO$_2X^1$ or —N$X^2X^3$, in which $X^1$, $X^2$ and $X^3$ independently of one another represent hydrogen, or represent methyl, ethyl, n- or i-propyl or n-, i-, s- or t-butyl, each of which is optionally substituted by fluorine, chlorine, bromine, cyano, hydroxyl, amino, methoxy, ethoxy, methylthio, ethylthio, methylsulfinyl, ethylsulfinyl, methylsulfonyl or ethylsulfonyl (which are in each case optionally substituted by fluorine and/or chlorine), or represent cyclopropyl, cyclobutyl, cyclopentyl or cyclohexyl, each of which is optionally substituted by fluorine, chlorine, bromine, cyano, carboxyl, phenyl (which is optionally substituted by fluorine, chlorine, bromine, cyano, methyl, ethyl, n- or i-propyl, n-, i-, s- or t-butyl, trifluoromethyl, methoxy, ethoxy, n- or i-propoxy, difluoromethoxy or trifluoromethoxy), methyl, ethyl, n- or i-propyl, methoxy-carbonyl or ethoxy-carbonyl, or represent in each case optionally substituted phenyl, naphthyl, furyl, tetrahydrofuryl, benzofuryl, tetrahydropyranyl, thienyl, benzothienyl, pyrrolyl, dihydropyrrolyl, tetrahydropyrrolyl, benzopyrrolyl, benzodihydropyrrolyl, oxazolyl, benzoxazolyl, isoxazolyl, thiazolyl, benzothiazolyl, isothiazolyl, imidazolyl, benzimidazolyl, oxadiazolyl, thiadiazolyl, pyridinyl, pyrimidinyl, pyridazinyl, pyrazinyl, 1,2,3-triazinyl, 1,2,4-triazinyl or 1,3,5-triazinyl, the substituents which are possible preferably being selected from the list which follows:

oxygen (as a replacement for two geminal hydrogen atoms), fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulfinyl, ethylsulfinyl, methylsulfonyl or ethylsulfonyl, trifluoromethyl, difluoromethoxy, trifluoromethoxy, difluoromethylthio, trifluoromethylthio, trifluoromethylsulfinyl or trifluoromethylsulfonyl, methylamino, ethylamino, n- or i-propylamino, dimethylamino, diethylamino, acetyl, propionyl, acetyloxy, methoxycarbonyl, ethoxycarbonyl, methylsulfonyloxy, ethylsulfonyloxy, hydroximinomethyl, hydroximinoethyl, methoximinomethyl, ethoximinomethyl, methoximinoethyl or ethoximinoethyl; or trimethylene (propane-1,3-diyl), methylenedioxy or ethylenedioxy, each of which is optionally monosubstituted or polysubstituted by identical or different substituents from the series consisting of fluorine, chlorine, methyl, ethyl and n- or i-propyl; or cyclopropyl, cyclobutyl, cyclopentyl or cyclohexyl, and also phenyl, phenoxy, benzyl or benzyloxy, each of which is optionally monosubstituted or polysubstituted in the phenyl moiety by identical or different substituents from the series consisting of fluorine, chlorine, bromine, cyano, methyl, ethyl, n- or i-propyl, n-, i-, s- or t-butyl, trifluoromethyl, methoxy, ethoxy, n- or i-propoxy, difluoromethoxy or trifluoromethoxy, or $X^2$ and $X^3$ together with the nitrogen atom form a 5-, 6- or 7-membered heterocycle which optionally contains one or two further hetero atoms, such as nitrogen, oxygen and/or sulfur, $Y^1$ represents hydrogen, or represents methyl, ethyl, n- or i-propyl or n-, i-, a- or t-butyl, each of which is optionally substituted by fluorine, chlorine, bromine, cyano, hydroxyl, amino, methoxy, ethoxy, methylthio, ethylthio, methylsulfinyl, ethylsulfinyl, methylsulfonyl or ethylsulfonyl (which are in each case optionally substituted by fluorine and/or chlorine), or represents cyclopropyl, cyclobutyl, cyclopentyl or cyclohexyl, each of which is optionally substituted by fluorine, chlorine, bromine, cyano, carboxyl, phenyl (which is optionally substituted by fluorine, chlorine, bromine, cyano, methyl, ethyl, n- or i-propyl, n-, i-, s- or t-butyl, trifluoromethyl, methoxy, ethoxy, n- or i-propoxy, difluoromethoxy or trifluoromethoxy), methyl, ethyl, n- or i-propyl, methoxy-carbonyl or ethoxy-carbonyl, or represents in each case optionally substituted phenyl, naphthyl, furyl, tetrahydrofuryl, benzofuryl, tetrahydropyranyl, thienyl, benzothienyl, pyrrolyl, dihydropyrrolyl, tetrahydropyrrolyl, benzopyrrolyl, benzodihydropyrrolyl, oxazolyl, benzoxazolyl, isoxazolyl, thiazolyl, benzothiazolyl, isothiazolyl, imidazolyl, benzimidazolyl, oxadiazolyl, thiadiazolyl, pyridinyl, pyrimidinyl, pyridazinyl, pyrazinyl, 1,2,3-triazinyl, 1,2,4-triazinyl or 1,3,5-triazinyl, the substituents which are possible preferably being selected from the list which follows:

oxygen (as a replacement for two geminal hydrogen atoms), fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, -ethoxy, n- or i-propoxy, methylthio, ethylthio, n- or i-propylthio, methylsulfinyl, ethylsulfinyl, methylsulfonyl or ethylsulfonyl, trifluoromethyl, difluoromethoxy, trifluoromethoxy, difluoromethylthio, trifluoromethylthio, trifluoromethylsulfinyl or trifluoromethylsulfonyl, methylamino, ethylamino, n- or i-propylamino, dimethylamino, diethylamino, acetyl, propionyl, acetyloxy, methoxycarbonyl, ethoxycarbonyl, methyl-sulfonyloxy, ethylsulfonyloxy, hydroximinomethyl, hydroximinoethyl, methoximinomethyl, ethoximinomethyl, methoximinoethyl or ethoximinoethyl; or trimethylene (propane-1,3-diyl), methylenedioxy or ethylenedioxy, each of which is optionally monosubstituted or polysubstituted by identical or different substituents from the series consisting of fluorine, chlorine, methyl, ethyl and n- or i-propyl; or cyclopropyl, cyclobutyl, cyclopentyl or cyclohexyl, and also phenyl, phenoxy, benzyl or benzyloxy, each of which is optionally monosubstituted or polysubstituted in the phenyl moiety by identical or different substituents from the series consisting of fluorine, chlorine, bromine, cyano, methyl, ethyl, n- or i-propyl, n-, i-, s- or t-butyl, trifluoromethyl, methoxy, ethoxy, n- or i-propoxy, difluoromethoxy or trifluoromethoxy, Z represents methyl, ethyl, n- or i-propyl or n-, i-, s- or t-butyl, each of which is optionally substituted by fluorine, chlorine, bromine, cyano, hydroxyl, amino, methoxy, ethoxy, methylthio, ethylthio, methylsulfinyl, ethylsulfinyl, methylsulfonyl or ethylsulfonyl (which are in each case optionally substituted by fluorine and/or chlorine), or represents allyl, crotonyl, 1-methyl-allyl, propargyl or 1-methyl-propargyl, each of which is optionally substituted by fluorine, chlorine or bromine, or represents cyclopropyl, cyclobutyl, cyclopentyl or cyclohexyl, each of which is optionally substituted by fluorine, chlorine, bromine, cyano, carboxyl, phenyl (which is optionally substituted by fluorine, chlorine, bromine, cyano, methyl, ethyl, n- or i-propyl, n-, i-, s- or t-butyl, trifluoromethyl, methoxy, ethoxy, n- or i-propoxy, difluoromethoxy or trifluoromethoxy)methyl, ethyl, n- or i-propyl, methoxy-carbonyl or ethoxy-carbonyl, or represents in each case optionally substituted phenyl, naphthyl, furyl, tetrahydrofuryl, benzofuryl, tetrahydropyranyl, thienyl, benzothienyl, pyrrolyl, dihydropyrrolyl, tetrahydropyrrolyl, benzopyrrolyl, benzodihydropyrrolyl, oxazolyl, benzoxazolyl, isoxazolyl, thiazolyl, benzthiazolyl, isothiazolyl, imidazolyl, benzimidazolyl, oxadiazolyl, thiadiazolyl, pyridinyl, pyrimidinyl, pyridazinyl, pyrazinyl, 1,2,3-triazinyl, 1,2,4-triazinyl or 1,3,5-triazinyl, phenyloxy, naphthyloxy, furyloxy, tetrahydrofuryloxy, benzofuryloxy, tetrahydropyranyloxy, thienyloxy, benzothienyloxy, pyrrolyloxy, dihydropyrrolyloxy, tetrahydropyrrolyloxy, benzopyrrolyloxy, benzodihydropyrrolyloxy, oxazolyloxy, benzoxazolyloxy, isoxazolyloxy, thiazolyloxy, benzthiazolyloxy, isothiazolyloxy, imidazolyloxy, benzimidazolyloxy, oxadiazolyloxy, thiadiazolyloxy, pyridinyloxy, pyrimidinyloxy, pyridazinyloxy, pyrazinyloxy, 1,2,3-triazinyloxy, 1,2,4-triazinyloxy or 1,3,5-triazinyloxy, phenylthio, naphthylthio, furylthio, tetrahydrofurylthio, benzofurylthio, tetrahydropyranylthio, thienylthio, benzothienylthio, pyrrolylthio, dihydropyrrolylthio, tetrahydropyrrolylthio, benzopyrrolylthio, benzodihydropyrrolylthio, oxazolylthio, benzoxazolylthio, isoxazolylthio, thiazolylthio, benzthiazolylthio, isothiazolylthio, imidazolylthio, benzimidazolylthio, oxadiazolylthio, thiadiazolylthio, pyridinylthio, pyrimidinylthio, pyridazinylthio, pyrazinylthio, 1,2,3-triazinylthio, 1,2,4-triazinylthio or 1,3,5-triazinylthio, phenylamino, naphthylamino, furylamino, tetrahydrofurylamino, benzofurylamino, tetrahydropyranylamino, thienylamino, benzothienylamino, pyrrolylamino, dihydropyrrolylamino, tetrahydropyrrolylamino, benzopyrrolylamino, benzodihydropyrrolylamino, oxazolylamino, benzoxazolylamino, isoxazolylamino, thiazolylamino, benzthiazolylamino, isothiazolylamino, imidazolylamino, benzimidazolylamino, oxadiazolylamino, thiadiazolylamino, pyridinylamino, pyrimidinylamino, pyridazinylamino, pyrazinylamino, 1,2,3-triazinylamino, 1,2,4-triazinylamino or 1,3,5-triazinylamino, the substituents which are possible preferably being selected from the list which follows:

oxygen (as a replacement for two geminal hydrogen atoms), fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulfinyl, ethylsulfinyl, methylsulfonyl or ethylsulfonyl, trifluoromethyl, difluoromethoxy, trifluoromethoxy, difluoromethylthio, trifluoromethylthio, trifluoromethylsulfinyl or trifluoromethylsulfonyl, methylamino, ethylamino, n- or i-propylamino, dimethylamino, diethylamino, acetyl, propionyl, acetyloxy, methoxycarbonyl, ethoxycarbonyl, methyl-sulfonyloxy, ethylsulfonyloxy, hydroximinomethyl, hydroximinoethyl, methoximinomethyl, ethoximinomethyl, methoximinoethyl or ethoximinoethyl; or trimethylene (propane-1,3-diyl), methylenedioxy or ethylenedioxy, each of which is optionally monosubstituted or polysubstituted by identical or different substituents from the series consisting of fluorine, chlorine, methyl, ethyl and n- or i-propyl; or cyclopropyl, cyclobutyl, cyclopentyl or cyclohexyl, and also phenyl, phenoxy, benzyl or benzyloxy, each of which is optionally monosubstituted or polysubstituted in the phenyl moiety by identical or different substituents from the series consisting of fluorine, chlorine, bromine, cyano, methyl, ethyl, n- or i-propyl, n-, i-, s- or t-butyl, trifluoromethyl, methoxy, ethoxy, n- or i-propoxy, difluoromethoxy or trifluoromethoxy.

A particularly preferred group of compounds according to the invention are those compounds of the formula (I), in which Ar represents ortho-phenylene, pyridine-2,3-diyl or thiophene-2,3-diyl, E represents one of the groups which follow

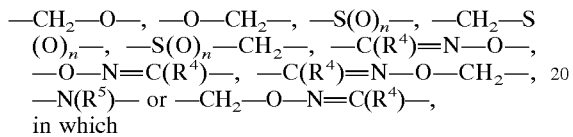

in which
R¹ and R² in each case represent methoxy,

G represents oxygen, methylene or one of the groups which follow
—CH₂—O—, —O—CH₂—, —S(O)ₙ—, —CH₂—S(O)ₙ—, —S(O)ₙ—CH₂—, —C(R⁴)=N—O—, —O—N=C(R⁴)—, —C(R⁴)=N—O—CH₂—, —N(R⁵)— or —CH₂—O—N=C(R⁴)—, in which
n represents the numbers 0, 1 or 2,
R⁴ represents hydrogen, methyl or ethyl,
R⁵ represents hydrogen, methyl or ethyl, X represents the groups —OX¹, —SX¹, —SOX¹, —SO₂X¹ or —NX²X³, in which X¹, X² and X³ independently of one another represent hydrogen, or represent methyl, ethyl, n- or i-propyl or n-, i-, s- or t-butyl, each of which is optionally substituted by fluorine, chlorine, cyano, hydroxyl, amino, methoxy, methylthio (which are in each case optionally substituted by fluorine and/or chlorine), or represent cyclopropyl, cyclobutyl, cyclopentyl or cyclohexyl, each of which is optionally substituted by fluorine, chlorine, bromine, cyano, carboxyl, phenyl (which is optionally substituted by fluorine, chlorine, methyl, trifluoromethyl or trifluoromethoxy), methyl, ethyl, n- or i-propyl, methoxycarbonyl or ethoxycarbonyl, or represents in each case optionally substituted phenyl, pyridinyl, pyrimidinyl, pyridazinyl, pyrazinyl, 1,2,3-triazinyl, 1,2,4-triazinyl or 1,3,5-triazinyl, the substituents which are possible preferably being selected from the list which follows:

fluorine, chlorine, bromine, cyano, methyl, ethyl, n- or i-propyl, n-, i-, s- or t-butyl, methoxy, ethoxy, n- or i-propoxy, methylthio, ethylthio,- n- or i-propylthio, methylsulfinyl, ethylsulfinyl, methylsulfonyl or ethylsulfonyl, trifluoromethyl, difluoromethoxy, trifluoromethoxy, difluoromethylthio, trifluoromethylthio, trifluoromethylsulfinyl or trifluoromethylsulfonyl, -methoxycarbonyl, ethoxycarbonyl, methoximinomethyl, ethoximinomethyl, methoximinoethyl or ethoximinoethyl, or methylenedioxy or ethylenedioxy, each of which is optionally monosubstituted or polysubstituted by identical or different substituents from the series consisting of fluorine, chlorine, methyl or ethyl, or phenyl, phenoxy, benzyl or benzyloxy, each of which is optionally monosubstituted or polysubstituted in the phenyl moiety by identical or different substituents from the series consisting of fluorine, chlorine, bromine, cyano, methyl, ethyl, n- or i-propyl, n-, i-, s- or t-butyl, trifluoromethyl, methoxy, ethoxy, n- or i-propoxy, difluoromethoxy or trifluoromethoxy, or X² and X³ together form a pyrazole, imidazole or triazole ring which is optionally substituted as above, Y¹ represents hydrogen, or represents methyl, ethyl, n- or i-propyl or n-, i-, s- or t-butyl, each of which is optionally substituted by fluorine, chlorine, cyano, hydroxyl, amino, methoxy, methylthio (which are in each case optionally substituted by fluorine and/or chlorine), or represents cyclopropyl, cyclobutyl, cyclopentyl or cyclohexyl, each of which is optionally substituted by fluorine, chlorine, bromine, cyano, carboxyl, phenyl (which is optionally substituted by fluorine, chlorine, methyl, trifluoromethyl or trifluoromethoxy), methyl, ethyl, n- or i-propyl, methoxycarbonyl or ethoxycarbonyl, or represents in each case optionally substituted phenyl, pyridinyl, pyrimidinyl, pyridazinyl, pyrazinyl, 1,2,3-triazinyl, 1,2,4-triazinyl or 1,3,5-triazinyl, the substituents which are possible preferably being selected from the list which follows: fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulfinyl, ethylsulfinyl, methylsulfonyl or ethylsulfonyl, trifluoromethyl, difluoromethoxy, trifluoromethoxy, difluoromethylthio, trifluoromethylthio, trifluoromethylsulfinyl or trifluoromethylsulfonyl, methoxycarbonyl, ethoxycarbonyl, methoximinomethyl, ethoximinomethyl, methoximinoethyl or ethoximinoethyl, or methylenedioxy or ethylenedioxy, each of which is optionally monosubstituted or polysubstituted by identical or different substituents from the series consisting of fluorine, chlorine, methyl or ethyl, or phenyl, phenoxy, benzyl or benzyloxy, each of which is optionally monosubstituted or polysubstituted in the phenyl moiety by identical or different substituents from the series consisting of fluorine, chlorine, bromine cyano, methyl, ethyl, n- or i-propyl, n-, i-, s- or t-butyl, trifluoromethyl, methoxy, ethoxy, n- or i-propoxy, difluoromethoxy or trifluoromethoxy, Z represents in each case optionally substituted phenyl, pyridinyl, pyrimidinyl, pyridazinyl, pyrazinyl, 1,2,3-triazinyl, 1,2,4-triazinyl or 1,3,5-triazinyl, phenyloxy, pyridinyloxy, pyrimidinyloxy, pyridazinyloxy, pyrazinyloxy, 1,2,3-triazinyloxy, 1,2,4-triazinyloxy or 1,3,5-triazinyloxy, phenylthio, pyridinylthio, pyrimidinylthio, pyridazinylthio, pyrazinylthio, 1,2,3-triazinylthio, 1,2,4-triazinylthio or 1,3,5-triazinylthio, phenylamino, pyridinylamino, pyrimidinylamino, pyridazinylamino, pyrazinylamino, 1,2,3-triazinylamino, 1,2,4-triazinylamino or 1,3,5-triazinylamino, the substituents which are possible preferably being selected from the list which follows: fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulfinyl, ethylsulfinyl, methylsulfonyl or ethylsulfonyl, trifluoromethyl, difluoromethoxy, trifluoromethoxy, difluoromethylthio, trifluoromethylthio, trifluoromethylsulfinyl or trifluoromethylsulfonyl, methoxycarbonyl, ethoxycarbonyl, methoximinomethyl, ethoximinomethyl, methoximinoethyl or ethoximinoethyl, or methylenedioxy or ethylenedioxy, each of which is optionally monosubstituted or polysubstituted by identical or different substituents from the series consisting of fluorine, chlorine, methyl or ethyl, or phenyl, phenoxy, benzyl or benzyloxy, each of which is optionally monosubstituted or polysubstituted in the phenyl moiety by identical or different substituents from the series consisting of fluorine, chlorine, bromine, cyano, methyl, ethyl, n- or i-propyl, n-, i-, s- or t-butyl, trifluoromethyl, methoxy, ethoxy, n- or i-propoxy, difluoromethoxy or trifluoromethoxy.

The abovementioned definitions of radicals, in general or in preferred ranges, apply to the end products of the formula (I) and, analogously, to the starting materials or intermediates required in each case for their preparation.

These definitions of radicals can be combined with each other as desired, that is to say combinations between the abovementioned ranges of preferred compounds are also possible.

If, for example, methyl [2-(2-methylphenoxymethyl)-phenyl]-2-methoximinothioacetate and O-methyl-hydroxylammonium chloride are used as starting substances, the course of the reaction of process (a) according to the invention can be outlined by the following equation:

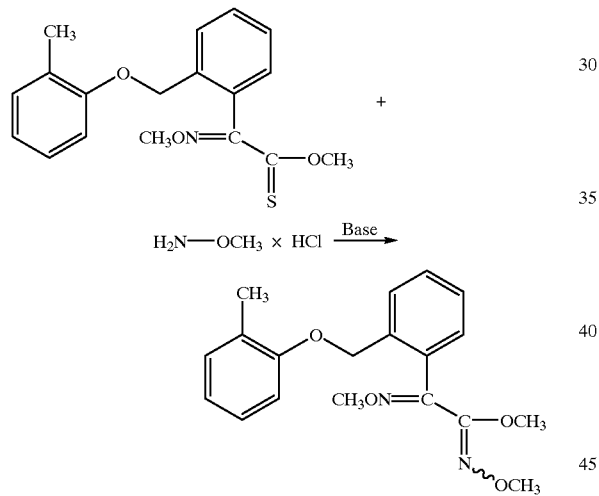

If, for example, N-methyl-{2-[1-(3-trifluoromethylphenyl)-ethylideneaminoxymethyl]-phenyl}-2-methoximinothioacetamide is used as starting substance, methyl iodide as the alkylating agent and O-methylhydroxylammonium chloride as further starting substance, the course of the reaction of process (b) according to the invention can be outlined by the following equation:

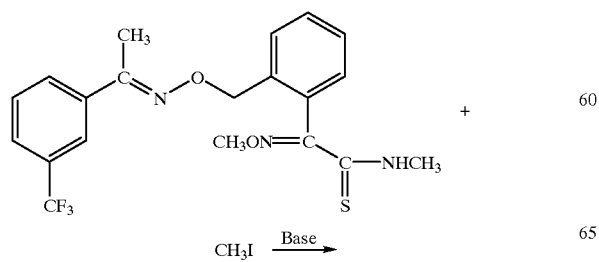

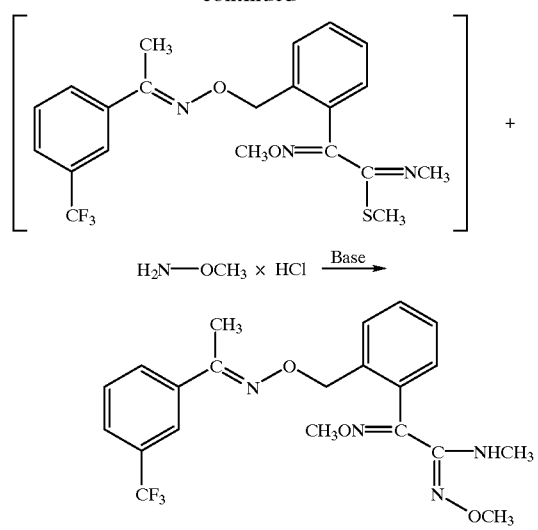

If, for example, N-methoxy-[2-(2-methylphenoxymethyl)-phenyl]-2-methoximinothioacetamide is used as starting substance, methyl iodide as alkylating agent and dimethylamine as further starting substance, the course of the reaction of process (c) according to the invention can be outlined by the following equation:

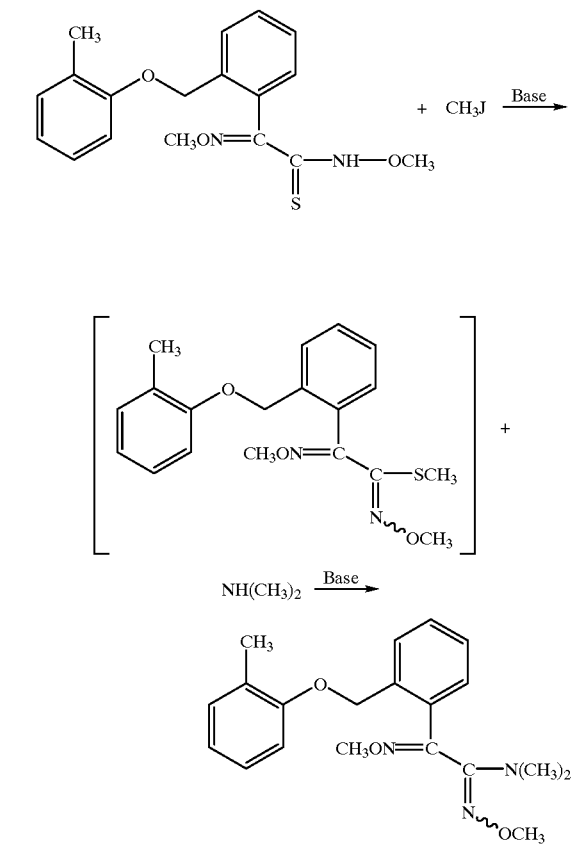

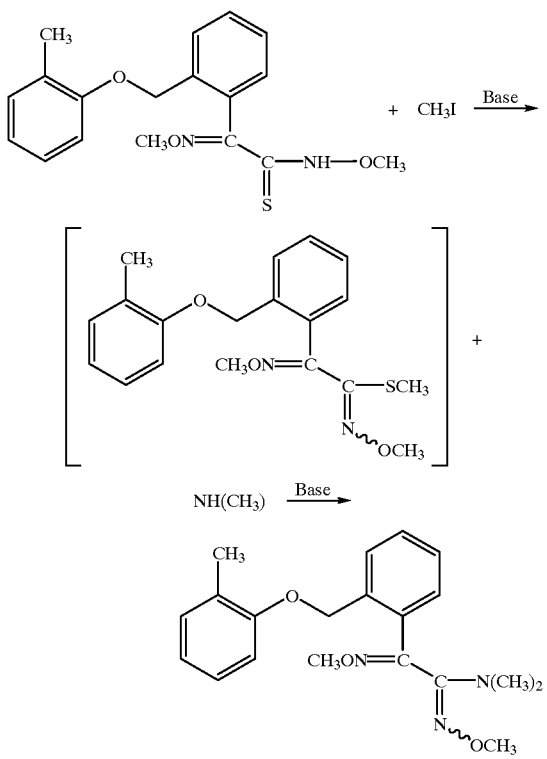

Formula (II) provides a general definition of the thiocarbonyl derivatives required as starting substances for carrying out process (a) according to the invention. In formula (II), Ar, E, G, $X^1$ and Z preferably, or in particular, have those meanings which have already been mentioned above in connection with the description of the compounds of the formula (I) as being preferred, or particularly preferred, for these substituents.

The thiocarbonyl derivatives of the formula (II) are known (cf., for example, EP-A-432 503) or can be obtained by standard methods described in the literature, for example by reacting the corresponding keto derivatives of the general formula (VII)

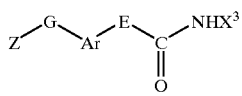

(VII)

in which

Ar, E, G, $X^1$ and Z have the abovementioned meanings, with a sulfurizing agent such as, for example, $P_4S_{10}$ or Lawesson reagent [2,4-bis(4-methoxyphenyl)-1,3,2,4-dithiadiphosphetane-2,4-dithione] at temperatures between 80 and 200° C., if appropriate in a diluent such as, for example, xylene or toluene (cf. also the preparation examples).

The keto derivatives of the formula (VII) are known or can be obtained by known methods (cf. in this context, for example, EP-A 253 213, EP-A 254 426, EP-A 299 694, EP-A 432 503, EP-A 460 575).

Formula (III) provides a general definition of the hydroxylamine derivatives furthermore required as starting substances for carrying out processes (a) and (b) according to the invention. In formula (III), $Y^1$ preferably, or in particular, has those meanings which have already been mentioned above in connection with the description of the compounds of the formula (I) as being preferred, or particularly preferred, for this substituent.

The hydroxylamine derivatives of the formula (III) and their acid addition salts such as, for example, their hydrochlorides and hydroacetates, are generally known compounds of organic chemistry or can be obtained by standard methods described in the literature.

Formula (IV) provides a general definition of the amide derivatives required as starting substances for carrying out process (b) according to the invention. In formula (IV), Ar, E, G, $X^3$ and Z preferably, or in particular, have those meanings which have already been mentioned above in connection with the description of the compounds of the formula (I) as being preferred, or particularly preferred, for these substituents.

The amide derivatives of the formula (IV) are as yet not known from the literature. However, they can be obtained by standard methods described in the literature, for example by reacting the corresponding keto derivatives of the general formula (VIII)

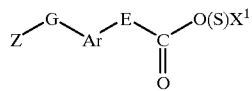

(VIII)

in which

Ar, E, G, $X^3$ and Z have the abovementioned meanings, with a sulfurizing agent such as, for example, $P_4S_{10}$ or Lawesson reagent [2,4-bis(4-methoxyphenyl)-1,3,2,4-dithiadiphosphetane-2,4-dithione] at temperatures between 80 and 200° C., if appropriate in a diluent such as, for example, xylene or toluene (cf. also the preparation examples).

The keto derivatives of the formula (VIII) are known or can be obtained by known methods (cf. in this context, for example, WO-A 92/13 830) by reacting, for example, keto derivatives of the general formula (VII) with suitable amines.

Suitable alkylating agents for carrying out processes (b) and (c) according to the invention are customary reagents such as, for example, alkyl halides, in particular methyl chloride, methyl bromide and methyl iodide, and also dialkyl sulfates, in particular dimethyl sulfate. The alkylating agents are generally known compounds of organic chemistry.

Formula (V) provides a general definition of the amide derivatives required as starting substances for carrying out process (c) according to the invention. In formula (V), Ar, E, G, $Y^1$ and Z preferably, or in particular, have those meanings which have already been mentioned above in connection with the description of the compounds of the formula (I) as being preferred, or particularly preferred, for these substituents.

The amide derivatives of the formula (V) are as yet not known from the literature. However, they can be obtained by standard methods described in the literature, for example by reacting the corresponding keto derivatives of the general formula (IX)

$$Z\diagdown_{\text{Ar}}\diagup^{\text{G}}\diagdown_{\text{Ar}}\diagup^{\text{E}}\diagdown_{\underset{\underset{\text{O}}{\|}}{\text{C}}}\diagup^{\text{NH}-\text{O}-\text{Y}^1} \quad (\text{IX})$$

in which

Ar, E, G, $Y^1$ and Z have the abovementioned meanings, with a sulfurizing agent such as, for example, $P_4S_{10}$ or Lawesson reagent [2,4-bis(4-methoxyphenyl)-1,3,2,4-dithiadiphosphetane-2,4-dithione] at temperatures between 80 and 200° C., if appropriate in a diluent such as, for example, xylene or toluene.

The keto derivatives of the formula (IX) are as yet not known from the literature. However, they can be obtained by standard methods described in the literature, for example by reacting methyl esters of the formula (VII) ($X^1$=$CH_3$) with hydroxylamine derivatives of the formula (III) in accordance with process (a).

Suitable diluents for carrying out processes (a) to (c) according to the invention are inert organic solvents. The following can preferably be used: aliphatic, alicyclic or aromatic, optionally halogenated hydrocarbons such as, for example, benzine, benzene, toluene, xylene, chlorobenzene, petroleum ether, hexane, cyclohexane, dichloromethane, chloroform, carbon tetrachloride, ethers such as diethyl ether, dioxane, tetrahydrofuran, ethylene glycol dimethyl ether or ethylene glycol diethyl ether, nitriles such as acetonitrile or propionitrile, amides such as dimethylformamide, dimethylacetamide, N-methylformanilide, N-methylpyrrolidone or hexamethylphosphoramide, esters such as ethyl acetate, or sulfoxides such as dimethyl sulfoxide, alcohols such as methanol or ethanol, or basic solvents such as pyridine or triethylamine.

Processes (a) and (b) according to the invention are preferably carried out in the presence of a suitable reaction auxiliary. Suitable reaction auxiliaries are all inorganic and organic bases which are conventionally used. The following are preferably used: alkali metal hydrides, alkali metal hydroxides, alkali metal alcoholates, alkali metal carbonates or alkali metal hydrogen carbonates such as, for example, sodium hydroxide, sodium methylate, sodium ethylate, potassium t-butylate, sodium carbonate, potassium carbonate or sodium hydrogen carbonate, or else tertiary amines such as, for example, triethylamine, N,N-dimethylaniline, pyridine, N,N-dimethylaminopyridine, diazabicyclooctane (DABCO), diazabicyclonones (DNB) or diazabicycloundecene (DBU). Acidic reaction auxiliaries such as, for example, p-toluenesulfonic acid, may be advantageous.

When carrying out processes (a) to (c) according to the invention, the reaction temperatures can be varied within a substantial range. In general, the processes are carried out at temperatures between 0° C. and +200° C., preferably at temperatures between 20° C. and 150° C.

To carry out processes (a) to (c) according to the invention, 1 to 4 mol, preferably 1 to 2 mol, of hydroxylamine derivative of the formula (III) or amine of the formula (VI) and, if appropriate 1 to 3 mol, preferably 1 to 2 mol, of reaction auxiliary, and, if appropriate, 1 to 10 mol, preferably 1 to 5 mol, of alkylating agent are generally employed per mol of thiocarbonyl derivative of the formula (II) or amide derivative of the formula (IV) or amide derivative of the formula (V), respectively.

The reactions are carried out and the reaction products are worked up and isolated by generally customary methods (cf. also the preparation examples).

The active compounds according to the invention have a potent microbicidal activity and can be employed in practice for combating undesired microorganisms. The active compounds are suitable for use as plant protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation:

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubense;*

Plasmopara species, such as, for example, *Plasmopara viticola;*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, synonym Helminthosporium);

Cochliobolus species, such as, for example, *Cochliobolus sativus* (conidia form: Drechslera, synonym Helminthosporium);

Uromyces species, such as, for example, *Uromyces appendiculatus;*

Puccinia species, such as, for example, *Puccinia recondita;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae* and

Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The active compounds according to the invention can be employed particuarly successfully for combating diseases in fruit and vegetable growing, such as, for example, against Sphaerotheca, Podosphaera and Venturia species, for combating cereal diseases, such as, for example, against Erysiphe species, or for combating rice diseases such as, for example, against *Pyricularia oryzae*. Besides, the active compounds according to the invention have a good in-vitro activity.

Depending on their particular physical and/or chemical properties, the active compounds can be converted to the customary formulations, such as solutions, emulsions, suspensions, powders, foams, pastes, granules, aerosols, very fine capsules in polymeric substances and in coating compositions for seed, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulfoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be used as such or, in their formulations, also in the form of a mixture with known fungicides, bactericides, acaricides, nematicides or insecticides, for example to widen the spectrum of action or to prevent build-up of resistance.

The following are suitable examples for use in mixtures:
Fungicides
2-aminobutane; 2-anilino-4-methyl-6-cyclopropylpyrimidine; 2',6'-dibromo-2-methyl-4'-trifluoromethoxy-4'-trifluoro-methyl-1,3-thiazole-5-carboxanilide; 2,6-dichloro-N-(4-trifluoromethylbenzyl) benzamide; (E)-2-methoxyimino-N-methyl-2-(2-phenoxyphenyl)-acetamide; 8-hydroxyquinoline sulfate; methyl (E)-2-{(2-[6-(2-cyanophenoxy)-pyrimidin-4-yloxy]phenyl}3-methoxyacrylate; methyl (E)-methoximino[alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulfide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazole, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetylaluminum, fthalide, fuberidazole, furalaxyl, furmecyclox, guazatine, hexachlorobenzene, hexaconazole, hymexazole, imazalil, imibenconazole, iminoctadine, iprobenfos (IBP), iprodione, isoprothiolane, kasugamycin, copper preparations such as: copper hydroxide, copper naphthenate, copper oxychloride, copper sulfate, copper oxide, oxinecopper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothalisopropyl, nuarimol, ofurace, oxadixyl, oxamocarb, oxycarboxin, perfurazoate, penconazole, pencycuron, phosdiphen, pimaricin, piperalin, polyoxin, probenazole, prochloraz, procymidone, propamocarb, propiconazole, propineb, pyrazophos, pyrifenox, pyrimethanil, pyroquilon, quintozene (PCNB), sulfur and sulfur preparations, tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforine, triticonazole, validamycin A, vinclozolin, zineb, ziram
Bactericides
bronopol, dichlorophen, nitrapyrin, nickel dimethyldithiocarbamate, kasugamycin, octhilinone, furanecarboxylic acid, oxytetracyclin, probenazole, streptomycin, tecloftalam, copper sulfate and other copper preparations
Insecticides/Acaricides/Nematicides
abamectin, AC 303 630, acephate, acrinathrin, alanycarb, aldicarb, alphamethrin, amitraz, avermectin, AZ 60541, azadirachtin, azinphos A, azinphos M, azocyclotin, Bacillus thuringiensis, bendiocarb, benfuracarb, bensultap, beta-cyluthrin, bifenthrin, BPMC, brofenprox, bromophos A, bufencarb, buprofezin, butocarboxin, butylpyridaben, cadusafos, carbaryl, carbofuran, carbophenothion, carbosulfan, cartap, CGA 157 419, CGA 184699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton M, demeton S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etofenprox, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mevinphos, mesulfenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemeton M, oxydeprofos, parathion A, parathion M, permethrin, phenthoate, phorate, phosalone, phosmet, phosphamidon, phoxim, pirimicarb, pirimiphos K, pirimiphos A, profenofos, promecarb, propaphos, propoxur, prothiofos, prothoate, pymetrozin, pyraclofos, pyridaphenthion, pyresmethrin, pyrethrum, pyridaben, pyrimidifen, pyriproxifen, quinalphos, RH 5992, salithion, sebufos, silafluofen, sulfotep, sulprofos, tebufenozid, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, YI 5301/5302, zetamethrin.

A mixture with other known active compounds, such as herbicides, or with fertilizers and growth regulators is also possible.

The active compounds can be employed as such, in the form of their formulations or in the use forms prepared therefrom, such as ready-to-use solutions, suspensions, wettable powders, pastes, soluble powders, dusts and granules. They are applied in the customary manner, for example by pouring, spraying, atomizing, scattering, dusting, foaming, brushing on and the like. It is furthermore possible to apply the active compounds by the ultra-low-volume method or to inject the preparation of active compound, or the active compound itself, into the soil. The seed of the plants can also be treated.

In the treatment of parts of plants, the active compound concentrations in the use forms can be varied within a substantial range: they are generally between 1 and 0.0001% by weight, preferably between 0.5 and 0.001% by weight.

In the treatment of seed, amounts of active compound of 0.001 to 50 g are generally required per kilogram of seed, preferably 0.01 to 10 g.

In the treatment of the soil, active compound concentrations of 0.00001 to 0.1% by weight, preferably 0.0001 to 0.02% by weight, are required at the site of action.

PREPARATION EXAMPLES

Example 1

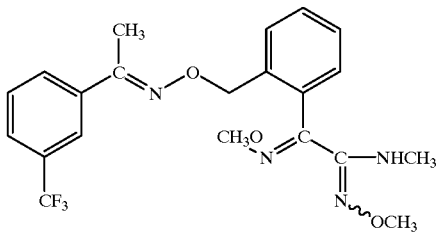

Process b 1.4 g (3.3 mmol) of N-methyl-{2-[(1-(3-trifluoromethylphenyl)ethylidene)-aminooxymethyl]-phenyl}-2-methoximinothioacetamide in 10 ml of dimethylformamide are stirred for 3 hours at 40° C. together with 1.5 g (10.8 mmol) of potassium carbonate and 2 g (14 mmol) of methyl iodide. A mixture of 1.1 g (13.1 mmol) of O-methylhydroxylammonium chloride in 5 ml of methanol and 1.8 ml of 2-molar sodium methylate solution is added to this mixture, and the reaction mixture is refluxed for 30 minutes. The reaction mixture is then poured into water and extracted using diethyl ether, and, after the solvent has been stripped off, the residue is chromatographed in diethyl ether:petroleum ether=1:1.

0.7 g (48.5% of theory) of 1,2-bis(methoximino)-1-methylamino-2-{2-[(1-(3-trifluoromethylphenyl)ethylidene)-aminooxymethyl]-phenyl}-ethane is obtained.

$^1$H NMR (CDCl$_3$/tetramethylsilane): 100 δ=2.283 (3H); 2.824/2.842 (3H); 3.788 (3H); 3.978 (3H); 5.019/5.037 (1H); 5.215 (2H); 7.2–7.6 (6H); 7.757/7.784 (1H); 7.847 (1H) ppm.

Preparation of the Starting Material (II-1)

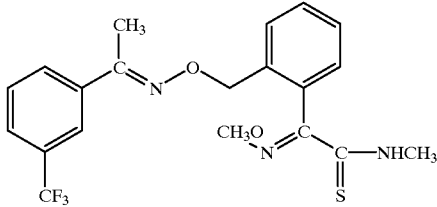

3 g (7.36 mmol) of N-methyl-{2-[1-(3-trifluoromethylphenyl)ethylidene)-aminooxymethyl]phenyl}-2-methoximinoacetamide are refluxed for 15 minutes together with 0.4 g of P$_4$S$_{10}$ in 30 ml of toluene. The mixture is filtered, the filtrate is concentrated, and the residue is chromatographed in diethyl ether:petroleum ether=1:1.

2 g (64% of theory) of N-methyl-{2-[1-(3-trifluoromethylphenyl)ethylidene)-aminooxymethyl]phenyl}-2-methoximinothioacetamide are obtained.

$^1$H NMR (CDCl$_3$/tetramethylsilane): 100 δ=2.222 (3H); 3.207/3.224 (3H); 3.956 (3H); 5.125 (2H); 7.0–8.0 (8H); 8.65 (1H) ppm.

Example 2

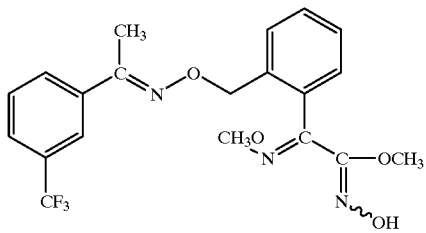

Process a 6.7 ml of 2-molar sodium methylate solution are added dropwise to 0.93 g (13.4 mmol) of hydroxylammonium chloride in 7 ml of methanol. 4.5 g (10.6 mmol) of methyl{2-[(1-(3-trifluoromethylphenyl)ethylidene)-aminooxymethyl]-phenyl}-2-methoximino-thioacetate are added, and the mixture is refluxed for 15 minutes. The reaction mixture is allowed to stand for 24 hours at room temperature, the methanol is stripped off in vacuo, and the residue is partitioned between water and ethyl acetate. After the solvent has been stripped off, the product is chromatographed in diethyl ether:petroleum ether=1:1.

2.7 g (60.1% of theory) of 1-hydroximino-1-methoxy-2-methoximino-2-{2-[(1-(3-trifluoromethylphenyl) ethylidene)-aminooxymethyl]-phenyl}ethane are obtained.

$^1$H NMR (CDCl$_3$/tetramethylsilane): 100 δ=2.199 (3H); 3.949 (3H); 4.003 (3H); 5.114 (2H); 7.0–7.6 (6H); 7.7–7.9 (2H) ppm.

Example 3

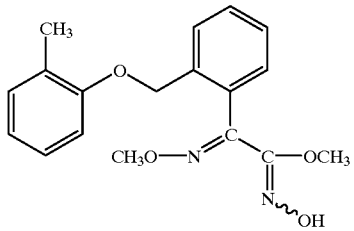

Process a 12 ml of a 2-molar solution of sodium methylate in methanol are added to 2 g (0.024 mol) of O-methylhydroxylammonium chloride in 12 ml of methanol. 8.0 g (0.024 mol) of methyl[2-(2-methylphenoxymethyl)-phenyl]-2-methoximino-thioacetate are added to this solution, and the mixture is refluxed for 15 minutes. The reaction mixture is allowed to stand for 24 hours at room temperature, the methanol is stripped off in vacuo, and the residue is partitioned between water and ethyl acetate. After the solvent has been stripped off, the residue is chromatographed in diethyl ether:petroleum ether=1:3.

2.1 g (25.5% of theory) of 1-methoxy-1,2-bis (methoximino)-2-(2-methylphenoxymethyl)phenyl-ethane are obtained.

$^1$H NMR (CDCl$_3$/tetramethylsilane): 100 δ=2.288 (3H); 3.761 (3H); 3.968 (3H); 3.980 (3H); 5.005 (2H); 6.783/6.811/6.842/6.866 (2H); 7.05–7.2 (2H); 7.3–7.5 (2H); 7.5–7.6 (1H) ppm.

Other examples of the compounds of the formula (I) which can be prepared analogously to the preparation examples and in accordance with the general descriptions of the processes according to the invention are those listed in Table 1 below:

Preparation of the Starting Material (II-2)

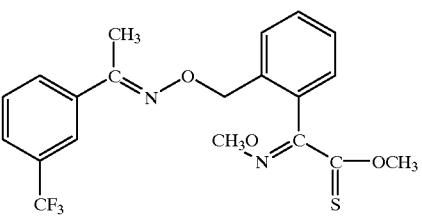

10 g (0.024 mol) of methyl{2-[(1-(3-trifluoromethyl-phenyl)ethylidene)-aminooxymethyl]-phenyl}-2-methoximinoacetate are refluxed for 16 hours in 50 ml of xylene together with 14.9 g (0.036 mol) of Lawesson reagent. Then, a further 14.9 g (0.036 mol) of Lawesson reagent are added, and the mixture is refluxed for a further 16 hours. The mixture is concentrated, and the residue is chromatographed in petroleum ether:tert-butyl methyl ether=4:1.

4.2 g (40.4% of theory) of methyl{2-[(1-(3-trifluoromethylphenyl)ethylidene)-aminooxymethyl]-phenyl}-2-methoximino-thioacetate are obtained.

GC/MS: M=424, 393, 362, 345, 317, 268, 240, 222, 208, 186, 145, 116, 89, 75, 47.

TABLE 1

(I)

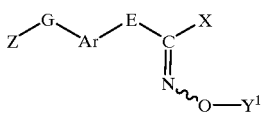

| Ex. No. | Z | G | Ar | E | X | Y$^1$ | Physical data |
|---|---|---|---|---|---|---|---|
| 4 | ![2-methylphenyl] | —OCH$_2$— | ![phenyl] | ![C=N-OCH$_3$] | —NHCH$_3$ | CH$_3$ | $^1$H NMR 2.29(s); 3.75(s) 3.96(s); 5.05(s) |

TABLE 1-continued $$Z-G-Ar-E-C(X)=N\sim O-Y^1 \quad (I)$$

| # | Z-G | | Ar | E | X | Y¹ | |
|---|---|---|---|---|---|---|---|
| 5 | 2-CH₃-C₆H₄- | —OCH₂— | 2-CH₃-C₆H₄- | >C(CH₃)=N—OCH₃ | —NHC₃H₇-i | CH₃ | ¹H NMR 1.08(d); 2.03(s); 3.76(s); 3.96(s); 5.04(s) |
| 6 | 2-CH₃-C₆H₄- | —OCH₂— | 2-CH₃-C₆H₄- | >C(CH₃)=N—OCH₃ | —NHC₂H₅ | CH₃ | ¹H NMR 1.06(t); 2.29(s); 3.76(s); 3.96(s); 5.04(s) |
| 7 | 2-CH₃-C₆H₄- | —OCH₂— | 2-CH₃-C₆H₄- | — | —NH₂ | CH₃ | ¹H NMR 3.87(s); 4.97(s, br) |
| 8 | 4-CH₃-C₆H₄- | —OCH₂— | 2-CH₃-C₆H₄- | — | —NH₂ | CH₃ | ¹H NMR 3.87(s); 5.14(s, br) |
| 9 | 2-OCH₃-C₆H₄- | —OCH₂— | 2-CH₃-C₆H₄- | — | —NH₂ | CH₃ | m.p. 83° C. |
| 10 | 2-Cl-C₆H₄- | —OCH₂— | 2-CH₃-C₆H₄- | — | —NH₂ | CH₃ | ¹H NMR 3.87(s); 5.02(s, br) |
| 11 | 2-Cl-5-CH₃-C₆H₃- | —OCH₂— | 2-CH₃-C₆H₄- | — | —NH₂ | CH₃ | m.p. 92–93° C. |
| 12 | 1-naphthyl | —OCH₂— | 2-CH₃-C₆H₄- | — | —NH₂ | CH₃ | ¹H NMR 3.87(s); 4.96 (s, br) |
| 13 | 2-C₂H₅-C₆H₄- | —OCH₂— | 2-CH₃-C₆H₄- | — | —NH₂ | CH₃ | ¹H NMR 3.67(s); 6.13 (s, br) |

TABLE 1-continued
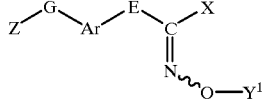
(I)
| Ex. No. | Z | G | Ar | E | X | Y | |
|---|---|---|---|---|---|---|---|
| 14 | 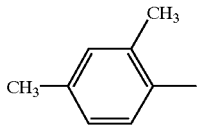 | —OCH$_2$— | 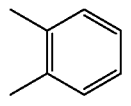 | — | —NH$_2$ | CH$_3$ | m.p. 61° C. |
| 15 | 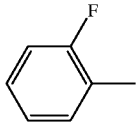 | —OCH$_2$— | 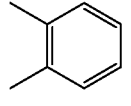 | — | —NH$_2$ | CH$_3$ | $^1$H NMR 3.86(s); 5.01 (s, br) |
| Ex. No. | Z | G | Ar | E | X | Y | $^1$H NMR (CDCl$_3$/TMS) |
|---|---|---|---|---|---|---|---|
| 16 | 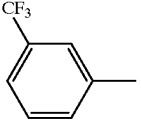 | 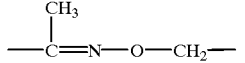 | 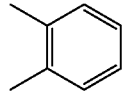 | — | —SO$_2$C$_2$H$_5$ | CH$_3$ | 4.14(s); |
| 17 | 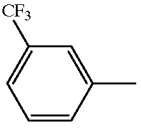 | 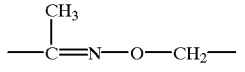 | 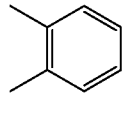 | — | —SOC$_2$H$_5$ | CH$_3$ | 3.99(s); |
| 18 | 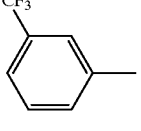 | 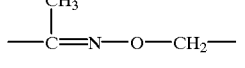 | 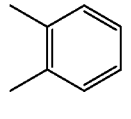 | — |  | CH$_3$ | 4.04(s); |
| 19 | 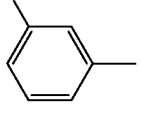 | 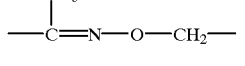 | 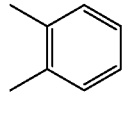 | — | —SC$_2$H$_5$ | CH$_3$ | 4.04(s); |
| 20 | 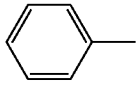 | —OCH$_2$— | 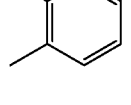 | — | —NH$_2$ | CH$_3$ | 3.87(s); |
| 21 | 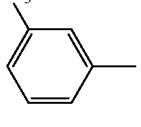 | —OCH$_2$— | 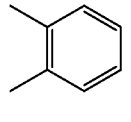 | — | —NH$_2$ | CH$_3$ | 3.86(s); |
| 22 | 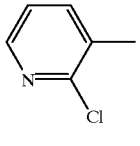 | —OCH$_2$— | 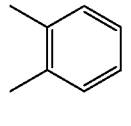 | — | —NH$_2$ | CH$_3$ | 3.87(s); |

TABLE 1-continued (I)

$$Z-G-Ar-E-\underset{\underset{\underset{O-Y^1}{\overset{|}{N}}}{\overset{||}{C}}}{\overset{X}{|}}$$

| 23 | 3,5-dimethylphenyl | —OCH₂— | o-tolyl | — | —NH₂ | CH₃ 3.88(s); |
| 24 | 2,3-dimethylphenyl | —OCH₂— | o-tolyl | — | —NH₂ | CH₃ 3.87(s); |
| 25 | 2,3,4-trimethylphenyl | —OCH₂— | o-tolyl | — | —NH₂ | CH₃ 3.89(s); |
| 26 | 2-methyl-4-isopropylphenyl | —OCH₂— | o-tolyl | — | —NH₂ | CH₃ 3.9(s); |

Example 16

25 g (0.0609 mol) of

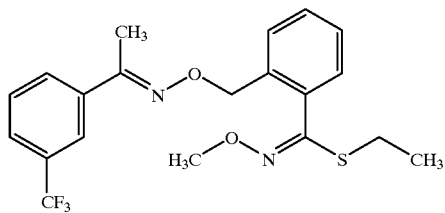

are stirred for 12 hours at room temperature together with 28.9 g of 80% strength 3-chloroperoxybenzoic acid (0.134 mol) in 244 ml of dichloromethane. The solid constituents are filtered off, the filtrate is concentrated, and the residue is chromatographed on silica gel using diethyl ether:petroleum ether=1:1. After the eluent has been stripped off, 13 g (48.2% of theory) are obtained.

Example 17

2.9 g (0.00707 mol) of

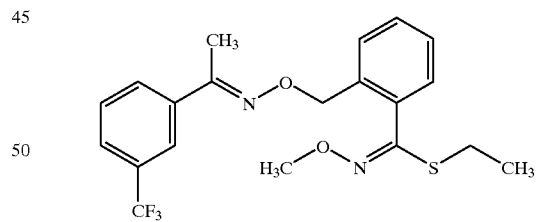

dissolved in 60 ml of methanol are added dropwise to a solution of 2.2 g (0.00358 mol) of oxone in 16 ml of water. The mixture is stirred for 4 hours at room temperature, the methanol is stripped off, the residue is extracted using ethyl acetate, the ethyl acetate is stripped off, and the residue is chromatographed on silica gel using diethyl ether. After the eluent has been stripped off, 1.6 g (53.1% of theory) are obtained.

Example 18

0.136 g (0.0020 mol) of imidazole are dissolved in 2 ml of dimethylformamide. After 0.12 g (0.002 mol) of 40% strength sodium hydride have been added, the mixture is stirred for 10 minutes at room temperature, and 0.88 g (0.002 mol) of

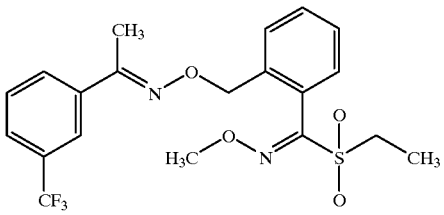

are added. The mixture is allowed to stand for 2 days at room temperature, then poured into water and extracted using ethyl acetate, the solvent is stripped off, and 0.75 g (90% of theory) are obtained.

Preparation of the Starting Materials

Example 19

10 g (0.0273 mol) of

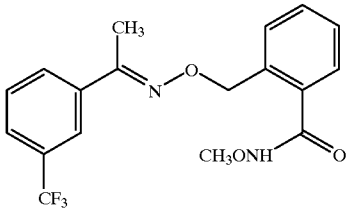

in 50 ml of toluene are refluxed for 10 minutes together with 2.4 g (0.00539 mol) of phosphorus pentasulfide. The sludgy precipitate is removed by decanting, and the liquid phase is concentrated in vacuo. The crude intermediate

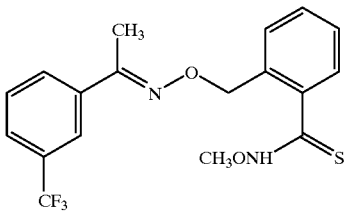

is immediately combined with 7.6 g (0.055 mol) of potassium carbonate and 4.2 g (0.0272 mol) of diethyl sulfate in 55 ml of acetone and the mixture is stirred for 2 hours at room temperature. After the acetone has been stripped off, the residue is chromatographed on silica gel using diethyl ether:petroleum ether=1:3. After the eluent has been stripped off, 3 g (26.8% of theory) are obtained.

Example 19a

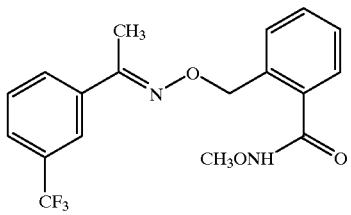

10 g (0.0296 mol) of

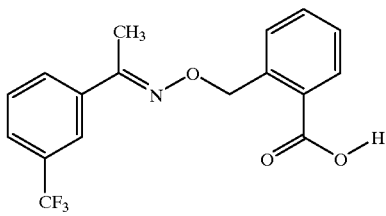

dissolved in 100 ml of diethyl ether are poured into 6.2 g (0.0298 mol) of phosphorus pentachloride, and the mixture is stirred for 10 minutes at room temperature. This solution is poured into a mixture of 5 g (0.06-mol) of O-methylhydroxylamine hydrochloride, 30 g (0.217 mol) of potassium carbonate, 100 g of ice and 50 g of water. The mixture is stirred vigorously for 15 minutes, and the ether phase is separated off and reextracted using ether. After the solvent has been stripped off, 10.25 g of 80% pure crystals (75% of theory) are obtained.

Example 19b

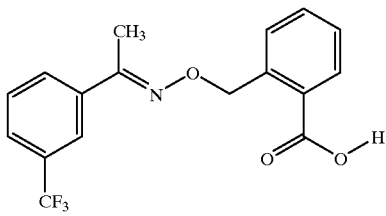

27 g (0.0769 mol) of

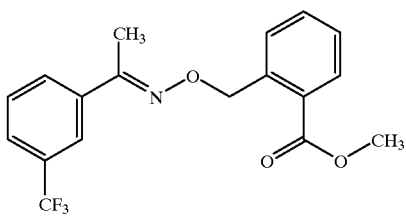

are dissolved in 150 ml of methanol, 13.7 g (0.154 mol) of 45% strength aqueous sodium hydroxide solution are added, and the mixture is stirred for 1 hour at 60° C. The methanol is stripped off, the mixture is acidified using hydrochloric acid, and the acid is extracted using dichloromethane. After the solvent has been stripped off, 20.8 g (80.2% of theory) crystallize.

Example 19c 9.8 g (0.087 mol) of potassium tert-butylate are dissolved in 90 ml of dimethylformamide. 17.7 g (0.087 mol) of 3-trifluoromethylacetophosphenone oxime are added at 0° C., followed by 20 g (0.087 mol) of methyl 2-bromoethylbenzoate. The mixture is subsequently stirred for two hours at room temperature, dimethylformamide is distilled off in vacuo and the residue is partitioned between ethyl acetate and water. The ethyl acetate is stripped off, whereupon 29.6 g (96.5% of theory) of

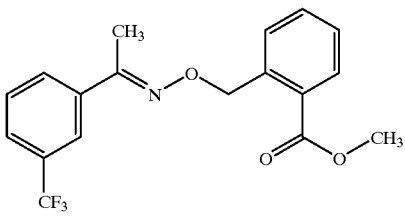

are obtained, an ester which can be distilled at 170 to 175° C. at 0.5 torr.

Standard Examples

Example D
Pyricularia Test (Rice)/Protective
  Solvent: 12.5 parts by weight of acetone
  Emulsifier: 0.3 part by weight of alkyl-aryl polyglycol ether
  To produce a suitable preparation of active compound, 1 part by weight of active compound is mixed with the stated amounts of solvent, and the concentrate is diluted with water and the stated amount of emulsifier to the desired concentration.
  To test for protective activity, young rice plants are sprayed with the preparation of active compound until dripping wet. After the spray coating has dried on, the plants are inoculated with an aqueous spore suspension of Pyricularia oryzae. The plants are then placed in a greenhouse at 100% relative atmospheric humidity and 25° C.
  Evaluation of the disease infestation is carried out 4 days after the inoculation.
  In this test, a degree of effectiveness of 89% is shown, for example, by the compound of Preparation Example 4 at an active compound concentration of 0.025%.

Example E
Erysiphe Test (Wheat)/Curative
  Solvent: 10 parts by weight of N-methyl-pyrrolidone
  Emulsifier: 0.6 part by weight of alkyl-aryl polyglycol ether
  To produce a suitable preparation of active compound, 1 part by weight of active compound is mixed with the stated amounts of solvent and emulsifier, and the concentrate is diluted with water to the desired concentration.
  To test for curative activity, young plants are dusted with spores of Erysiphe graminis f. sp. tritici. 48 hours after the inoculation, the plants are sprayed with the preparation of active compound at the application rate given.
  The plants are placed in a greenhouse at a temperature of about 20° C. and a relative atmospheric humidity of about 80%, in order to promote the development of powdery mildew pustules.
  Evaluation is carried out 7 days after the inoculation.
  In this test, a degree of effectiveness of 100% is shown, for example, by the compound of Preparation Example 4 at an active compound concentration of 250 g/ha.

Example F
Erysiphe Test (Barley)/Curative
  Solvent: 10 parts by weight of N-methyl-pyrrolidone
  Emulsifier: 0.6 part by weight of alkyl-aryl polyglycol ether
  To produce a suitable preparation of active compound, 1 part by weight of active compound is mixed with the stated amounts of solvent and emulsifier, and the concentrate is diluted with water to the desired concentration.
  To test for curative activity, young plants are dusted with spores of Erysiphe graminis f. sp. hordei. 48 hours after the inoculation, the plants are sprayed with the preparation of active compound at the application rate given.
  The plants are placed in a greenhouse at a temperature of about 20° C. and a relative atmospheric humidity of about 80%, in order to promote the development of powdery mildew pustules.
  Evaluation is carried out 7 days after the inoculation.
  In this test, a degree of effectiveness of 100% is shown, for example, by the compound of Preparation Example 4 at an active compound concentration of 250 g/ha.

Example G
Erysiphe Test (Wheat)/Protective
  Solvent: 10 parts by weight of N-methyl-pyrrolidone
  Emulsifier: 0.6 part by weight of alkyl-aryl polyglycol ether
  To produce a suitable preparation of active compound, 1 part by weight of active compound is mixed with the stated amounts of solvent and emulsifier, and the concentrate is diluted with water to the desired concentration.
  To test for protective activity, young plants are sprayed with the preparation of active compound at the application rate given.
  After the spray coating has dried on, the plants are dusted with spores of Erysiphe graminis f.sp. tritici.
  The plants are placed in a greenhouse at a temperature of about 20° C. and a relative atmospheric humidity of about 80%, in order to promote the development of powdery mildew pustules.
  Evaluation is carried out 7 days after the inoculation.
  In this test, a clearly superior activity compared with the prior art is shown, for example, by the compounds of the following Preparation Examples:
  In this test, a degree of effectiveness of 100% is shown, for example, by the compound of Preparation Example 4 at an active compound concentration of 250 g/ha.

Example H
Erysiphe Test (Barley)/Protective
  Solvent: 10 parts by weight of N-methyl-pyrrolidone
  Emulsifier: 0.6 part by weight of alkyl-aryl polyglycol ether
  To produce a suitable preparation of active compound, 1 part by weight of active compound is mixed with the stated amounts of solvent and emulsifier, and the concentrate is diluted with water to the desired concentration.
  To test for protective activity, young plants are sprayed with the preparation of active compound at the application rate given.
  After the spray coating has dried on, the plants are dusted with spores of Erysiphe graminis f.sp. hordei.
  The plants are placed in a greenhouse at a temperature of about 20° C. and a relative atmospheric humidity of about 80%, in order to promote the development of powdery mildew pustules.
  Evaluation is carried out 7 days after the inoculation.
  In this test, a clearly superior activity compared with the prior art is shown, for example, by the compounds of the following Preparation Examples:

In this test, a degree of effectiveness of 100%, is shown, for example, by the compound of Preparation Example 4 at an active compound concentration of 250 g/ha.

Example I
Sphaerotheca Test (Cucumber)/Protective
Solvent: 4.7 parts by weight of acetone
Emulsifier: 0.3 part by weight of alkyl-aryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are dusted with conidia of the fungus Sphaerotheca fuliginea.

The plants are then placed in a greenhouse at 23 to 24° C. and at a relative atmospheric humidity of about 75%.

Evaluation is carried out 10 days after the inoculation.

In this test, degrees of effectiveness up to 100% are shown, for example, by the compounds of Preparation Examples (2), (4) and (11).

Example K
Podosphaera Test (Apple)/Protective
Solvent: 4.7 parts by weight of acetone
Emulsifier: 0.3 part by weight of alkyl-aryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated by dusting with conidia of the causative organism of apple mildew (Podosphaera leucotricha).

The plants are then placed in a greenhouse at 23° C. and a relative atmospheric humidity of about 70%.

Evaluation is carried out 9 days after the inoculation.

In this test, degrees of effectiveness up to 100% are shown, for example, by the compounds of Preparation Examples (2), (4), (11) and (17).

Example L
Venturia Test (Apple)/Protective
Solvent: 4.7 parts by weight of acetone
Emulsifier: 0.3 part by weight of alkyl-aryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (*Venturia inaequalis*) and then remain in an incubation cabin at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, degrees of effectiveness of up to 100% are shown, for example, by the compounds of Preparation Examples (2), (4) and (11).

We claim:
1. An oxime derivative of the formula (I)

$$Z-G-Ar-E-C(X)=N-O-Y^1$$ (I)

in which
Ar represents optionally substituted phenylene the substituents being independently selected from the group consisting of:
halogen, cyano, nitro, amino, hydroxyl, formyl, carboxy, carbamoyl, thiocarbamoyl, in each case straight-chain or branched alkyl, alkoxy, alkylthio, alkylsulfinyl or alkylsulfonyl, in each case straight-chain or branched alkenyl, alkenyloxy, or alkinyloxy, in each case straight-chain or branched halogenoalkyl, halogenoalkoxy, halogenoalkylthio, halogenoalkylsufinyl or halogenoalkylsulfonyl, in each case straight-chain or branched halogenoalkenyl or halogenoalkenyloxy, in each case straight-chain or branched alkylamino, dialkylamino, alkylcarbonyl, alkylcarbonyloxy, alkoxycarbonyl, alkylsulfonyloxy, hydroximinoalkyl or alkoximinoalkyl, or represents in each case divalent alkylene or dioxyalkylene, each of which is optionally monosubstituted or polysubstituted by identical or different substituents selected from the group consisting of halogen and/or straight-chain or branched alkyl, and/or straight-chain or branched halogenoalkyl, E represents a 2-aza-1-alkene-1,1-diyl group, which has a radical $R^2$ in the 2-position;
where
$R^2$ represents hydrogen, or represents alkyl, alkoxy, alkylamino or dialkylamino, each of which is optionally substituted by halogen, cyano or alkoxy, and G represents —CH$_2$—O— or —O—CH$_2$—;
X represents —NX$^2$X$^3$,
where
$X^2$ and $X^3$ independently of one another represent hydrogen, or represent alkyl which is optionally substituted by halogen, cyano, hydroxyl, amino, or alkylthio, alkylsulfinyl or alkylsulfonyl, (which in each case are optionally substituted by halogen), or represent cycloalkyl which is optionally substituted by halogen, cyano, carboxyl, phenyl (which is optionally substituted by halogen, cyano, alkyl, halogenoalkyl, alkoxy or halogenoalkoxy), alkyl or alkoxycarbonyl, or represents in each case optionally substituted aryl, the substituents independently being selected from the group consisting of:
oxygen (as a replacement for two germinal hydrogen atoms), halogen, cyano, nitro, amino, hydroxyl, formyl, carboxyl, carbamoyl, thiocarbamoyl, in each case straight-chain or branched alkyl, alkoxy, alkylthio, alkylsulfinyl or alkylsulfonyl, in each case straight-chain or branched alkenyl or alkenyloxy, in each case straight-chain or branched halogenoalkyl, halogenoalkoxy, halogenoalkylthio, halogenoalkylsulfinyl or halogenoalkylsulfonyl, in each case straight-chain or branched halogenoalkenyl or halogenalkenyloxy, each case straight-chain or branched alkylamino, dialkylamino, alkylcarbonyl, alkylcarbonyloxy, alkoxycarbonyl, alkylsulfonyloxy, hydroximinoalkyl or alkoximinoalkyl, in each case divalent alkylene or dioxyalkylene, each of which is optionally mono- substituted or polysubstituted by identical or different substituents selected from the group consisting of halogen and/or straight-chain or branched alkyl, and/ or straight-chain or branched halogenoalkyl; or cycloalkyl, and also phenyl, phenoxy, benzyl, benzyloxy, phenylethyl or phenylethyloxy, each of which is optionally monosubstituted or polysubstituted in the phenyl moiety by identical or different substituents selected from the group consisting of halogen, cyano and/or straight-chain or branched alkyl and/or straight-chain or branched halogenoalkyl and/or straight-chain or branched alkoxy and/or straight-chain or branched halogenoalkoxy, $Y^1$ represents hydrogen, or represents alkyl which is optionally substituted by halogen, cyano, hydroxyl, amino, or alkyloxy, alkylthio, alkylsulfinyl or alkylsulfonyl, (which are in each case optionally substituted by halogen), or represents cycloalkyl which is optionally substituted by halogen, cyano, carboxyl, phenyl (which is optionally substituted by halogen, cyano, alkyl, halogenoalkyl, alkoxy or halogenoalkoxy), alkyl or alkoxycarbonyl, or represents in each case optionally substituted aryl, the substituents being independently selected from the group consisting of:

oxygen (as a replacement for two geminal hydrogen atoms), halogen, cyano, nitro, amino, hydroxyl, formyl, carboxyl, carbamoyl, thiocarbamoyl, in each case straight-chain or branched alkyl, alkoxy, alkylthio, alkylsulfinyl or alkylsulfonyl, in each case straight-chain or branched alkenyl or alkenyloxy, in each case straight-chain or branched halogenoalkyl, halogenoalkoxy, halogenoalkylthio, halogenoalkylsulfinyl or halogenoalkylsulfonyl, in each case straight-chain or branched halogenoalkenyl or halogenoalkenyloxy, in each case straight-chain or branched alkylamino, dialkylamino, alkylcarbonyl, alkylcarbonyloxy, alkoxycarbonyl, alkylsulfonyloxy, hydroximinoalkyl or alkoximinoalkyl, in each case divalent alkylene or dioxyalkylene, each of which is optionally monosubstituted or polysubstituted by identical or different substituents selected from the group consisting of halogen and/or straight-chain or branched alkyl, and/ or straight-chain or branched halogenoalkyl; or cycloalkyl, , and also phenyl, phenoxy, benzyl, benzyloxy, phenylethyl or phenylethyloxy, each of which is optionally monosubstituted or polysubstituted in the phenyl moiety by identical or different substituents, selected from the group consisting of halogen, cyano and/or straight-chain or branched alkyl and/or straight-chain or branched halogenoalkyl and/or straight-chain or branched alkoxy and/or straight-chain or branched halogenoalkoxy, and Z represents optionally substituted phenyl or naphthyl, the substituents being selected from the group consisting of:

oxygen (as a replacement for two geminal hydrogen atoms), halogen, cyano, nitro, amino, hydroxyl, formyl, carboxyl, carbamoyl, thiocarbamoyl, in each case straight-chain or branched alkyl, alkoxy, alkylthio, alkylsulfinyl or alkylsulfonyl, in each case straight-chain or branched alkenyl or alkenyloxy, in each case straight-chain or branched halogenoalkyl, halogenoalkoxy, halogenoalkylthio, halogenoalkylsulfinyl or halogenoalkylsulfonyl, in each case straight-chain or branched halogenoalkenyl or halogenalkenyloxy, in each case straight-chain or branched alkylamino, dialkylamino, alkylcarbonyl, alkylcarbonyloxy, alkoxycarbonyl, alkysulfonyloxy, hydroximinoalkyl or alkoximinoalkyl, in each case divalent alkylene or dioxyalkylene, each of which is optionally monosubstituted or polysubstituted by identical or different substituents selected from the group consisting of halogen and/or straight-chain or branched alkyl, and/or straight-chain or branched halogenoalyl; or cycloalkyl, and also phenyl, phenoxy, benzyl, benzyloxy, phenylethyl or phenylethyloxy, each of which is optionally monosubstituted or polysubstituted in the phenyl moiety by identical or different substituents selected from the group consisting of halogen, cyano and/or straight-chain or branched alkyl and/or straight-chain or branched halogenoalkyl and/or straight-chain or branched alkoxy and/or straight-chain or branched halogenoalkoxy;

said halogen containing derivatives having identical or different halogen atoms.

2. A compound of the formula (I) as claimed in claim 1, in which

Ar represents in each case optionally substituted phenylene, the substituents being selected from the group consisting of;

halogen, cyano, nitro, amino, hydroxyl, formyl, carboxy, carbamoyl, thiocarbamoyl, in each case straight-chain or branched alkyl, alkoxy, alkylthio, alkylsulfinyl or alkylsulfonyl, each of which has 1 to 6 carbon atoms, in each case straight-chain or branched alkenyl, alkenyloxy or alkinyloxy, each of which has 2 to 6 carbon atoms, in each case straight-chain or branched halogenoalkyl, halogenoalkoxy, halogenoalkylthio, halogenoalkylsulfinyl or halogenoalkylsulfonyl, each of which has 1 to 6 carbon atoms and 1 to 13 identical or different halogen atoms, in each case straight-chain or branched halogenoalkenyl or halogenoalkenyloxy, each of which has 2 to 6 carbon atoms and 1 to 13 identical or different halogen atoms, in each case straight-chain or branched alkylamino, dialkylamino, alkylcarbonyl, alkylcarbonyloxy, alkoxycarbonyl, alkylsulfonyloxy, hydroximinoalkyl or alkoximinoalkyl, each of which has 1 to 6 carbon atoms in the individual alkyl moieties, or represents in each case divalent alkylene or dioxyalkylene, each of which has 1 to 6 carbon atoms and each of which is optionally monosubstituted or polysubstituted by identical or different substituents of halogen and/or straight-chain or branched alkyl having 1 to 4 carbon atoms and/or straight-chain or branched halogenoalkyl having 1 to 4 carbon atoms and 1 to 9 identical or different halogen atoms, $R^2$ represents hydrogen, or represents alkyl, alkoxy, alkylamino or dialkylamino, each of which has 1 to 6 carbon atoms in the alkyl radicals and each of which is optionally substituted by halogen, cyano or $C_1$–$C_4$-alkoxy, and $X^2$ and $X^3$ independently of one another represent hydrogen, or represent alkyl having 1 to 8 carbon atoms which is optionally substituted by halogen, cyano, hydroxyl, amino, $C_1$–$C_4$-alkoxy, $C_1$–$C_4$-alkylthio, $C_1$–$C_4$-alkylsulfinyl or $C_1$–$C_4$-alkylsulfonyl (which are in each case optionally substituted by halogen), or represent cycloalkyl having 3 to 6 carbon atoms which is optionally substituted by halogen, cyano, carboxyl, phenyl (which is optionally substituted by halogen, cyano, $C_1$–$C_4$-alkyl, $C_1$–$C_4$-halogenoalkyl, $C_1$–$C_4$-alkoxy or $C_1$–$C_4$-halogenoalkoxy), $C_1$–$C_4$-alkyl or $C_1$–$C_4$-alkoxycarbonyl, or represent in each case optionally substituted phenyl or naphthyl the substituents independently being selected from the group consisting of:

oxygen (as a replacement for two geminal hydrogen atoms), halogen, cyano, nitro, amino, hydroxyl, formyl, carboxyl, carbamoyl, thiocarbamoyl, in each case straight-chain or branched alkyl, alkoxy, alkylthio, alkylsulfinyl or alkylsulfonyl, each of which has 1 to 6 carbon atoms, in each case straight-chain or branched alkenyl or alkenyloxy, each of which has 2 to 6 carbon atoms, in each case straight-chain or branched halogenoalkyl, halogenoalkoxy, halogenoalkylthio, halogenoalkylsulfinyl or halogenoalkylsulfonyl, each of which has 1 to 6 carbon atoms and 1 to 13 identical or different halogen atoms, in each case straight-chain or branched halogenoalkenyl or halogenoalkenyloxy, each of which has 2 to 6 carbon atoms and 1 to 13 identical or different halogen atoms, in each case straight-chain or branched alkylamino, dialkylamino, alkylcarbonyl, alkylcarbonyloxy, alkoxycarbonyl, alkylsulfonyloxy, hydroximinoalkyl or alkoximinoalkyl, each of which has 1 to 6 carbon atoms in the individual alkyl moieties, in each case divalent alkylene or dioxyalkylene, each of which has 1 to 6 carbon atoms and each of which is optionally monosubstituted or polysubstituted by identical or different substituents of halogen and/or straight-chain or branched alkyl having 1 to 4 carbon atoms and/or straight-chain or branched halogenoalkyl having 1 to 4 carbon atoms and 1 to 9 identical or different halogen atoms; or cycloalkyl having 3 to 6 carbon atoms, and also phenyl, phenoxy, benzyl, benzyloxy, phenylethyl or phenylethyloxy, each of which is optionally monosubstituted or polysubstituted in the phenyl moiety by identical or different substituents of of halogen, cyano and/or straight-chain or branched alkyl having 1 to 4 carbon atoms and/or straight-chain or branched halogenoalkyl having 1 to 4 carbon atoms and 1 to 9 identical or different halogen atoms and/or straight-chain or branched alkoxy having 1 to 4 carbon atoms and/or straight-chain or branched halogenoalkoxy having 1 to 4 carbon atoms and 1 to 9 identical or different halogen atoms, $Y^1$ represents hydrogen, or represents alkyl having 1 to 8 carbon atoms which is optionally substituted by halogen, cyano, hydroxyl, amino, $C_1$–$C_4$-alkoxy, $C_1$–$C_4$-alkylthio, $C_1$–$C_4$-alkylsulfinyl or $C_1$–$C_4$alkylsulfonyl (which are in each case optionally substituted by halogen), or represents cycloalkyl having 3 to 6 carbon atoms which is optionally substituted by halogen, cyano, carboxyl, phenyl (which is optionally substituted by halogen, cyano, $C_1$–$C_4$-alkyl, $C_1$–$C_4$-halogenoalkyl, $C_1$–$C_4$-alkoxy or $C_1$–$C_4$-halogenoalkoxy), $C_1$–$C_4$-alkyl or $C_1$–$C_4$-alkoxycarbonyl, or represents in each case optionally substituted phenyl, naphthyl, the substituents being independently selected from the group consisting of:

oxygen (as a replacement for two geminal hydrogen atoms), halogen, cyano, nitro, amino, hydroxyl, formyl, carboxyl, carbamoyl, thiocarbamoyl, in each case straight-chain or branched alkyl, alkoxy, alkylthio, alkylsulfinyl or alkylsulfonyl, each of which has 1 to 6 carbon atoms, in each case straight-chain or branched alkenyl or alkenyloxy, each of which ash 2 to 6 carbon atoms, in each case straight-chain or branched halogenoalkyl, halogenoalkoxy, halogenoalkylthio, halogenoalkylsulfinyl or halogenoalkylsulfonyl, each of which has 1 to 6 carbon atoms and 1 to 13 identical or different halogen atoms, in each case straight-chain or branched halogenoalkenyl or halogenoalkenyloxy, each of which has 2 to 6 carbon atoms and 1 to 13 identical or different halogen atoms, in each case straight-chain or branched alkylamino, dialkylamino, alkylcarbonyl, alkylcarbonyloxy, alkoxycarbonyl,, alkylsulfonyloxy, hydroximinoalkyl or alkoximinoalkyl, each of which has 1 to 6 carbon atoms in the individual alkyl moieties, in each case divalent alkylene or dioxyalkylene, each of which has 1 to 6 carbon atoms and each of which is optionally monosubstituted or polysubstituted by identical or different substituents from the series consisting of halogen and/or straight-chain or branched alkyl having 1 to 4 carbon atoms and/or straight-chain or branched halogenoalkyl having 1 identical or different substituents of halogen, cyano and/or straight-chain or branched alkyl having 1 to 4 carbon atoms and/or straight-chain or branched halogenoalkyl having 1 to 4 carbon atoms and 1 to 9 identical or different halogen atoms and/or straight-chain or branched alkoxy having 1 to 4 carbon atoms and 1 to 9 identical or different halogen atoms; or cycloalkyl having 3 to 6 carbon atoms, and also phenyl, phenoxy, benzyl, benzyloxy, phenylethyl or phenylethyloxy, each of which is optionally monosubstituted or polysubstituted in the phenyl moiety by identical or different substituents of halogen, cyano and/or straight-chain or branched alkyl having 1 to 4 carbon atoms and/or straight-chain or branched halogenoalkyl having 1 to 4 carbon atoms and 1 to 9 identical or different halogen atoms and/or straight-chain or branched alkoxy having 1 to 4 carbon atoms and/or straight chain or branched halogenoalkoxy having 1 to 4 carbon atoms and 1 to 9 identical or different halogen atoms, and Z represents optionally substituted phenyl or naphthyl, the substituents being selected from the group consisting of:

oxygen (as a replacement for two geminal hydrogen atoms), halogen, cyano, nitro amino, hydroxyl, formyl, carboxyl, carbamoyl, thiocarbamoyl, in each case straight-chain or branched alkyl, alkoxy, alkylthio, alkylsulfinyl or alkylsulfonyl, each of which has 1 to 6 carbon atoms, in each case straight-chain or branched alkenyl or alkenyloxy, each of which has 2 to 6 carbon atoms, in each case straight-chain or branched halogenoalkyl, halogenoalkoxy, halogenoalkylthio, halogenoalkylsulfinyl or halogenoalkylsulfonyl, each of which has 1 to 6 carbon atoms and 1 to 13 identical or different halogen atoms, in each case straight-chain or branched halogenoalkenyl or halogenoalkenyloxy, each of which has 2 to 6 carbon atoms and 1 to 13 identical or different halogen atoms, in each case straight-chain or branched alkylamino, dialkylamino, alkylcarbonyl, alkylcarbonyloxy, alkoxycarbonyl, alkylsulfonyloxy, hydroximinoalkyl or alkoximinoalkyl, each of which has 1 to 6 carbon atoms in the individual alkyl moieties, in each case divalent alkylene or dioxyalkylene, each of which has 1 to 6 carbon atoms and each of which is optionally monosubstituted or polysubstituted by identical or different substituents of halogen and/or straight-chain or branched alkyl having 1 to 4 carbon atoms and/or straight-chain or branched halogenoalkyl having 1 to 4 carbon atoms and 1 to 9 identical or different halogen atoms; or cycloalkyl having 3 to 6 carbon atoms, and also phenyl, phenoxy, benzyl, benzyloxy, phenylethyl or phenylethyloxy, each of which is optionally monosubstituted or polysubstituted in the phenyl moiety by identical or different substituents of halogen, cyano and/or straight-chain or branched alkyl having 1 to 4 carbon atoms and/or straight-chain or branched halogenoalkyl having 1 to 4 carbon atoms and 1 to 9 identical or different halogen atoms and/or straight-chain or branched alkoxy having 1 to 4 carbon atoms and/or straight-chain or branched halogenoalkoxy having 1 to 4 carbon atoms and 1 to 9 identical or different halogen atoms.

3. A compound of the formula (I) as claimed in claim 1, in which

Ar represents in each case optionally substituted ortho-, meta-, or para-phenylene, the substituents from the group consisting of:
fluorine, chlorine, cyano, methyl, ethyl, trifluoromethyl, methoxy, ethoxy, methylthio, methylsulfinyl or methylsulfonyl, $R^2$ represents hydrogen, or represents methyl, ethyl, methoxy, ethoxy, methylamino, ethylamino or dimethylamino, each of which is optionally substituted by fluorine, chlorine, cyano, methoxy or ethoxy, $X^2$ and $X^3$ independently of one another represent hydrogen, or represent methyl, ethyl, n- or i-propyl or n-, i-, s- or t-butyl, each of which is optionally substituted by fluorine, chlorine, bromine, cyano, hydroxyl, amino, or methoxy, ethoxy, methylthio, ethylthio, methylsulfinyl, ethylsulfinyl, methylsulfonyl or ethylsulfonyl (which are in each case optionally substituted by fluorine and/or chlorine or represent cyclopropyl, cyclobutyl, cyclopentyl or cyclohexyl, each of which is optionally substituted by fluorine, chlorine, bromine, cyano, carboxyl, phenyl (which is optionally substituted by fluorine, chlorine, bromine, cyano, methyl, ethyl, n- or i-propyl, n-, i-, s- or t-butyl trifluoromethyl, methoxy, ethoxy, n- or i-propoxy, difluoromethoxy or trifluoromethoxy), methyl, ethyl, n- or i-propyl, methoxy-carbonyl or ethoxy-carbonyl, or represent in each case optionally substituted phenyl, naphthyl, the substituents being selected from the group consisting of:
oxygen (as a replacement for two geminal hydrogen atoms), fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulfinyl, ethylsulfinyl, methylsulfonyl or ethylsulfonyl, trifluoromethyl, difluoromethoxy, trifluoromethoxy, difluoro-methylthio, trifluoromethylthio, trifluoromethylsulfinyl or trifluoromethylsulfonyl, methylamino, ethylamino, n- or i-propylamino, dimethylamino, diethylamino, acetyl, propionyl, acetyloxy, methoxycarbonyl, ethoxycarbonyl, methylsulfonyloxy, ethylsulfonyloxy, hydroximinomethyl, hydroximinoethyl, methoximinomethyl, ethoximinomethyl, methoximinomethyl or ethoximinomethyl; or trimethylene (propane-1,3-diyl), methylenedioxy or ethylenedioxy, each of which is optionally monosubstituted or polysubstituted by identical or different substituents of fluorine, chlorine, methyl, ethyl and n- or i-propyl; or cyclopropyl, cyclobutyl, cyclopentyl or cyclohexyl, and also phenyl, phenoxy, benzyl or benzyloxy, each of which is optionally monosubstituted or polysubstituted in the phenyl moiety by identical or different substituents of fluorine, chlorine, bromine, cyano, methyl, ethyl, n or i-propyl, n-, i-, s- or t-butyl, trifluoromethyl, methoxy, ethoxy, n- or i-propoxy, difluoromethoxy or trifluoromethoxy, $Y^1$ represents hydrogen, or represents methyl, ethyl, n- or i-propyl or n-, i-, s- or t-butyl, each of which is optionally substituted by fluorine, chlorine, bromine, cyano, hydroxyl, amino, methoxy, ethoxy, methylthio, ethylthio, methylsulfinyl, ethylsulfinyl, methylsulfonyl or ethylsulfonyl (which are in each case optionally substituted by fluorine and/or chlorine, or represents cyclopropyl, cyclobutyl, cyclopentyl or cyclohexyl, each of which is optionally substituted by fluorine, chlorine, bromine, cyano, carboxyl, phenyl (which is optionally substituted by fluorine, chlorine, bromine, cyano, methyl, ethyl, n- or i-propyl, n-, i-, s- or t-butyl, trifluoromethyl, methoxy, ethoxy, n- or i-propoxy, difluoromethoxy or trifluoromethoxy), methyl, ethyl, n- or i-propyl, methoxycarbonyl or ethoxy-carbonyl, or represents in each case optionally substituted phenyl, naphthyl, phenyloxy, naphthyloxy, phenylthio, naphthylthio, phenylamino or naphthylamino, the substituents being selected from the group consisting of:
oxy (as a replacement for two geminal hydrogen atoms), fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulfinyl, ethylsulfinyl, methylsulfonyl or ethylsulfonyl, trifluoromethyl, difluoromethoxy, trifluoromethoxy, difluoromethylthio, trifluoromethylthio, trifluoromethylsulfinyl or trifluoromethylsulfonyl, methylamino, ethylamino, n- or i-propylamino, dimethylamino, diethylamino, acetyl, propionyl, acetyloxy, methoxycarbonyl, ethoxycarbonyl, methylsulfonyloxy, ethylsulfonyloxy, hydroximinomethyl, hydroximinoethyl, methoximinomethyl, ethoximinomethyl, methoximinoethyl or ethoximinoethyl, or trimethylene (propane-1,3-diyl), methylenedioxy or ethylenedioxy, each of which is optionally monosubstituted or polysubstituted by identical or different substituents of fluorine, chlorine, methyl, ethyl and n- or i-propyl; or cyclopropyl, cyclobutyl, cyclopentyl or cyclohexyl, and also phenyl, phenoxy, benzyl or benzyloxy, each of which is optionally monosubstituted or polysubstituted in the phenyl moiety by identical or different substituents of fluorine, chlorine, bromine, cyano, methyl, ethyl, n- or i-propyl, n-, i-, s- or t-butyl, trifluoromethyl, methoxy, ethoxy, n- or i-propoxy, difluoromethoxy or trifluoromethoxy, and Z represents optionally substituted phenyl, the substituents being selected from the group consisting of:
oxygen (as a replacement for two geminal hydrogen atoms), fluorine, chlorine, bromine, cyano, nitro, amino, hydroxyl, formyl, carboxyl, carbamoyl, thiocarbamoyl, methyl, ethyl, n- or i-propyl, n- i-, s- or t-butyl, methoxy, ethoxy, n- or i-propoxy, methylthio, ethylthio, n- or i-propylthio, methylsulfinyl, ethylsulfinyl, methylsulfonyl or ethylsulfonyl, trifluoromethyl, difluoromethoxy, trifluoromethoxy, difluoromethylthio, trifluoromethylthio, trifluoromethylsulfinyl or trifluoromethylsulfonyl, methylamino, ethylamino, n- or i-propylamino, dimethylamino, diethylamino, acetyl, propionyl, acetyloxy, methoxycarbonyl, ethoxycarbonyl, methylsulfonyloxy, ethylsulfonyloxy, hydroximinomethyl, hydroximinoethyl, methoximinomethyl, ethoximinomethyl, methoximinoethyl or ethoximinoethyl; or trimethylene (propane-1,3-diyl), methylenedioxy or ethylenedioxy, each of which is optionally monosubstituted or polysubstituted by identical or different substituents of fluorine, chlorine, methyl, ethyl and n- or i-propyl; or cyclopropyl, cyclobutyl, cyclopentyl or cyclohexyl, and also phenyl, phenoxy, benzyl or benzyloxy, each of which is optionally monosubstituted or polysubstituted in the phenyl moiety by identical or different substituents of fluorine, chlorine, bromine, cyano, methyl, ethyl, n- or i-propyl, n-, i-, s- or t-butyl, trifluoromethyl, methoxy, ethoxy, n- or i-propoxy, difluoromethoxy or trifluoromethoxy.

4. A compound of the formula (I) as claimed in claim 1, where

Ar represents ortho-phenylene, $R^2$ represents methoxy, $X^2$ and $X^3$ independently of one another represent hydrogen, or represent methyl, ethyl, n- or i-propyl or n-, i-, s- or t-butyl, each of which is optionally substituted by fluorine, chlorine, cyano, hydroxy, amino, methoxy, methylthio (which are in each case optionally substituted by fluorine and/or chlorine), or represent cyclopropyl, cyclobutyl, cyclopentyl or cyclohexyl, each of which is optionally substituted by fluorine, chlorine, bromine, cyano, carboxyl, phenyl (which is optionally substituted by fluorine, chlorine, methyl, trifluoromethyl or trifluoromethoxy), methyl, ethyl, n- or i-propyl, methoxycarbonyl or ethoxycarbonyl, or represents in each case optionally substituted phenyl, the substituents being selected from the group consisting of:
fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulfinyl, ethylsulfinyl, methylsulfonyl or ethylsulfonyl, trifluoromethyl, difluoromethoxy, trifluoromethoxy, difluoromethylthio, trifluoromethylthio, trifluoromethylsulfinyl or trifluoromethylsulfonyl, methoxycarbonyl, ethoxycarbonyl, methoximinomethyl, ethoximinomethyl, methoximinoethyl or ethoximinoethyl, or methylenedioxy or ethylenedioxy, each of which is optionally monosubstituted or polysubstituted by identical or different substitutents of fluorine, chlorine, methyl, or ethyl, or phenyl, phenoxy, benzyl or benzyloxy, each of which is optionally monosubstituted or polysubstituted in the phenyl moiety by identical or different substituents of fluorine, chlorine, bromine, cyano, methyl, ethyl, n- or i-propyl n-, i-, s- or t-butyl, trifluoromethyl, methoxy, ethoxy, n- or 1-propoxy, difluoromethoxy or trifluoromethoxy, $Y^1$ represents hydrogen, or represents methyl, ethyl, n- or i-propyl or n-, i-, s- or t-butyl, each of which is optionally substituted by fluorine, chlorine, cyano, hydroxyl, amino, methoxy, methylthio (which are in each case optionally substituted by fluorine and/or chlorine), or represents cyclopropyl, cyclobutyl, cyclopentyl, or cyclohexyl, each of which is optionally substituted by fluorine, chlorine, bromine, cyano, carboxyl, phenyl (which is optionally substituted by fluorine, chlorine, methyl, trifluoromethyl or trifluoromethoxy), methyl, ethyl, n- or i-propyl, methoxycarbonyl or ethoxycarbonyl, or represents in each case optionally substituted phenyl, the substituents being selected from the group consisting of:
fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulfinyl, ethylsulfinyl, methylsulfonyl or ethylsulfonyl, trifluoromethyl, difluoromethoxy, trifluoromethyloxy, difluoromethylthio, trifluoromethylthio, trifluoromethylsulfinyl or trifluoromethylsulfonyl, methoxycarbonyl, ethoxycarbonyl, methoximinomethyl, ethoximinomethyl, methoximinoethyl or ethoximinoethyl, or methylenedioxy or ethylenedioxy, each of which is optionally monosubstituted or polysubstituted by identical or different substituents of fluorine, chlorine, methyl or ethyl, or phenyl, phenoxy, benzyl or benzyloxy, each of which is optionally monosubstituted or polysubstituted in the phenyl moiety by identical or different substituents of fluorine, chlorine, bromine, cyano, methyl, ethyl, n- or i-propyl, n-, i-, s-, or t-butyl, trifluoromethyl, methoxy, ethoxy, n- or i-propoxy, difluoromethoxy or trifluoromethoxy, and Z represents optionally substituted phenyl, the substituents being independently selected from the group consisting of:
fluorine, chlorine; bromine, cyano, methyl, ethyl, n- or i-propyl, i- s- or t-butyl, methoxy, ethoxy, n- or i-propoxy, methylthio, ethylthio, n- or i-propylthio, methylsulfinyl, ethylsulfinyl, methylsulfonyl, ethylsulfonyl or ethylsulfonyl, trifluoromethyl, difluoromethoxy, trifluoromethoxy, difluoromethylthio, trifluoromethylthio, trifluoromethylsulfinyl or trifluoromethylsulfonyl, methoxycarbonyl, ethoxycarbonyl, methoximinomethyl, ethoximinomethyl, methoximinoethyl or ethoximinoethyl, or methylenedioxy or ethylenedioxy, each of which is optionally monosubstituted or polysubstituted by identical or different substituents of fluorine, chlorine, methyl or ethyl, or phenyl, phenoxy, benzyl or benzyloxy, each of which is optionally monosubstituted or polysubsti tuted in the phenyl moiety by identical or different substituents of fluorine, chlorine, bromine, cyano, methyl, ethyl, n- or i-propyl, n-, i-, s-, or t-butyl, trifluoromethyl, methoxy, ethoxy, n- or i-propoxy, difluoromethoxy or trifluoromethoxy.

5. A method of combating pests comprising allowing compounds of formula (I) as claimed in claim 1 to act on pests and/or their environment.

6. A pesticidal composition comprising a pesticidally effective amount of a compound according to claim 1 and a diluent.

7. A pesticidal composition comprising a pesticidally effective amount of at least one compound according to claim 1 and at least one extender and/or surfactant.

* * * * *

UNITED STATES PATENT AND TRADEMARK OFFICE
CERTIFICATE OF CORRECTION

PATENT NO.    : 6,177,463 B1
DATED         : January 23, 2001
INVENTOR(S)   : Peter Gerdes et al.

It is certified that error appears in the above-identified patent and that said Letters Patent is hereby corrected as shown below:

<u>Column 45,</u>
Line 44, change "hydroxy" to -- hydroxyl --

Signed and Sealed this

Eighth Day of July, 2003

JAMES E. ROGAN
*Director of the United States Patent and Trademark Office*